United States Patent [19]

Kelly

[11] Patent Number: 5,238,600
[45] Date of Patent: Aug. 24, 1993

[54] IBIMETHYLENOXY CONTAINING LIQUID CRYSTAL COMPOUNDS

[75] Inventor: Stephen Kelly, Möhlen, Switzerland

[73] Assignee: Hoffmann-La Roche Inc., Nutley, N.J.

[21] Appl. No.: 346,190

[22] Filed: May 2, 1989

[30] Foreign Application Priority Data

Jun. 1, 1988 [CH] Switzerland ............ 2093/88
Mar. 10, 1989 [CH] Switzerland ............ 896/89

[51] Int. Cl.$^5$ ............ C09K 19/30; C09K 19/54; C07C 41/00; G02F 1/13
[52] U.S. Cl. ............ 252/299.63; 568/64.7; 568/661; 252/299.5; 252/299.61
[58] Field of Search ............ 252/299.61, 299.63, 252/299.5; 568/647, 661

[56] References Cited

U.S. PATENT DOCUMENTS

| | | | |
|---|---|---|---|
| 3,987,108 | 10/1976 | Karrer | 568/647 X |
| 4,035,056 | 7/1977 | Coates et al. | 252/299.66 X |
| 4,627,933 | 12/1986 | Eidenschink et al. | 252/299.6 |
| 4,676,604 | 6/1987 | Petrzilka | 359/103 X |
| 4,753,752 | 6/1988 | Raynes et al. | 252/299.65 |
| 4,886,620 | 12/1989 | Hopf et al. | 252/299.61 |
| 4,894,181 | 1/1990 | Praefcke et al. | 252/299.61 |
| 4,943,384 | 7/1990 | Sucrow et al. | 252/299.61 |
| 5,032,312 | 7/1991 | Kelly | 252/299.01 |

FOREIGN PATENT DOCUMENTS 122389 10/1984 European Pat. Off.
3509170 9/1986 Fed. Rep. of Germany.

OTHER PUBLICATIONS

Patent Abstract of Japan, vol. 11, No. 115 (C–415) 2562 p. 71 C 415.

Derwent E 15L03U11.

*Primary Examiner*—Robert L. Stoll
*Assistant Examiner*—Cynthia Harris
*Attorney, Agent, or Firm*—George M. Gould; George W. Johnston

[57] ABSTRACT

Compounds of the formula $$R^1-A^1-Z^1-A^2-(Z^2-A^3)_n-R^2 \qquad 1$$

wherein $Z^1$ denotes the group $-CH_2CH_2CH_2O-$ or $-OCH_2CH_2CH_2-$; n stands for the number 0 or 1; $R^1$ represents a group $R^3$ or $R^3-A^4-Z^3-$; $R^2$ represents a group $R^4$ or $R^4-A^5-Z^4-$; $Z^2$, $Z^3$ and $Z^4$ each independently are a single covalent bond. $-CH_2-CH_2-$, $-CH_2O-$, $-OCH_2-$, $-COO-$, $-OOC-$, $-CH_2CH_2CH_2O-$ or $-OCH_2CH_2CH_2-$; $A^1$, $A^2$, $A^3$, $A^4$ and $A^5$ each independently denote unsubstituted or methyl, halogen and/or cyano-substituted 1,4-phenylene, in which optionally 1–4 CH groups are replaced by nitrogen, unsubstituted or methyl- and/or cyano-substituted trans-1,4-cyclohexylene, in which optionally 2 $CH_2$ groups are replaced by oxygen and/or sulfur, bicyclo[2.2.2]-octane-1,4-diyl, 1,3,4-thiadiazole-2,5-diyl, naphthalene-2,6-diyl, tetralin-2,6-diyl or decalin-2,6-diyl; $R^3$ and $R^4$ each independently represent an unsubstituted or halogen- and/or cyano-substituted alkyl or alkenyl group, in which optionally 1 $CH_2$ group or 2 non-adjacent $CH_2$ groups is/are replaced by $-O-$, $-COO-$ and/or $-OOC-$, or one of the residues $R^3$ and $R^4$ also represents hydrogen, halogen, cyano or $-NCS$, as well as liquid crystalline mixtures and their use for electro-optical purposes.

23 Claims, No Drawings

IBIMETHYLENOXY CONTAINING LIQUID CRYSTAL COMPOUNDS

FIELD OF THE INVENTION

The present invention is concerned with novel compounds having a trimethylenoxy group, liquid crystalline mixtures which contain such compounds as well as their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to the person skilled in the art and can be based on various effects. Examples of such devices are cells having dynamic scattering, DAP cells (deformation of aligned phases), guest/host cells, TN cells ("twisted nematic") and STN cells ("super-twisted nematic") having a twisted nematic structure, SBE cells ("super-birefringence effect"), phase change cells having a cholesteric-nematic phase transition and OMI cells ("optical mode-interference"). The most common indicating devices are based on the Schadt-Helfrich effect and have a twisted nematic structure.

Further, electro-optical devices based on chiral tilted smectic liquid crystals are proposed in Appl. Phys. Lett. 36, 899 (1980) and in Recent Developments in Condensed Matter Physics 4, 309 (1981). In this case, the ferroelectric properties of these materials are made use of. As tilted smectic phases there are suitable, for example, smectic C, F. G, H, I and K phases. There are generally preferred smectic C phases, which permit especially large response speeds. The chiral tilted phases are usually denoted as $S_C^*$, $S_F^*$ etc., with the asterisk indicating the chirality.

The liquid crystal materials must have a good chemical and thermal stability and a high stability towards electric fields and electromagnetic radiation. Further, the liquid crystal materials should have a low viscosity and in the cells should give short response times, low threshold potentials and a high contrast. Furthermore, at usual operating temperatures they should have a suitable mesophase, for example a nematic, cholesteric or chiral tilted smectic phase. Other properties such as the electrical conductivity, the dielectric anisotropy and the optical anisotropy must fulfill different requirements depending on the type of cell and field of use. For example, materials for cells having a twisted nematic structure should have a positive dielectric anisotropy and an electrical conductivity which is as small as possible. In addition to the general interest in liquid crystal materials having a high optical anisotropy there has recently been an increased interest in materials having a low optical anisotropy, especially for actively addressed liquid crystal devices, for example, in TFT applications (thin film transistor) in television sets. On the other hand, chiral tilted smectic liquid crystals should have a sufficiently high spontaneous polarization.

In order to optimize the properties, liquid crystals are generally used as mixtures of several components. It is therefore important that the components have a good miscibility with one another. Cholesteric mixtures preferably include one or more optically active doping substances and a nematic liquid crystal material, and ferroelectric liquid crystals preferably include one or more optically active doping substances and a liquid crystal material having a tilted smectic phase.

SUMMARY OF THE INVENTION

The present invention provides the compounds of the formula

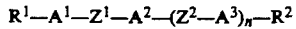

$$R^1-A^1-Z^1-A^2-(Z^2-A^3)_n-R^2 \qquad I$$

wherein $Z^1$ is a group —CH$_2$CH$_2$CH$_2$O— or —OCH$_2$CH$_2$CH$_2$—; n stands for the number 0 or 1; $R^1$ is a group $R^3$ or $R^3$—A$^4$—Z$^3$—; $R^2$ is a group $R^4$ or $R^4$—A$^5$—Z$^4$—; $Z^2$, $Z^3$ and $Z^4$ each independently are a single covalent bond, —CH$_2$—CH$_2$—, —CH$_2$O—, —OCH$_2$—, —COO—, —OOC—, —CH$_2$CH$_2$CH$_2$O— or —OCH$_2$CH$_2$CH$_2$—; A$^1$, A$^2$, A$^3$, A$^4$ and A$^5$ each independently are 1,4-phenylene unsubstituted or substituted with at least one of methyl, halogen or cyano, in which optionally 1-4 CH groups are replaced by nitrogen, trans-1,4-cyclohexylene unsubstituted or substituted with at least one of methyl or cyano, in which optionally 2 CH$_2$ groups are replaced by at least one of oxygen or sulfur, bicyclo[2.2.2]-octane-1,4-diyl, 1,3,4-thiadiazole-2,5-diyl, naphthalene-2,6-diyl, tetralin-2,6-diyl or decalin-2,6-diyl; $R^3$ and $R^4$ each independently are an alkyl or an alkenyl group, the alkyl and the alkenyl group being unsubstituted or substituted with at least one of halogen or cyano, in which optionally either 1 CH$_2$ group or 2 non-adjacent CH$_2$ groups is replaced by at least one of —O—, —COO— or —OOC—, or one of the groups of $R^3$ and $R^4$ is hydrogen, halogen, cyano or —NCS.

The invention is also concerned with liquid crystalline mixtures which contain compounds of formula I, as well as the use of such compounds for electro-optical purposes.

DETAILED DESCRIPTION OF PREFERRED EMBODIMENTS

The present invention provides the compounds of the formula

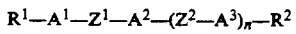

$$R^1-A^1-Z^1-A^2-(Z^2-A^3)_n-R^2 \qquad I$$

wherein $Z^1$ is a group —CH$_2$CH$_2$CH$_2$O— or —OCH$_2$CH$_2$CH$_2$—; n stands for the number 0 or 1; $R^1$ is a group $R^3$ or $R^3$—A$^4$—Z$^3$—; $R^2$ is a group $R^4$ or $R^4$—A$^5$—Z$^4$—; $Z^2$, $Z^3$ and $Z^4$ each independently are a single covalent bond, —CH$_2$—CH$_2$—, —CH$_2$O—, —OCH$_2$—, —COO—, —OOC—, —CH$_2$CH$_2$CH$_2$O— or —OCH$_2$CH$_2$CH$_2$—; A$^1$, A$^2$, A$^3$, A$^4$ and A$^5$ each independently are 1,4-phenylene unsubstituted or substituted with at least one of methyl, halogen or cyano, in which optionally 1-4 CH groups are replaced by nitrogen, trans-1,4-cyclohexylene unsubstituted or substituted with at least one of methyl or cyano, in which optionally 2 CH$_2$ groups are replaced by at least one of oxygen or sulfur, bicyclo[2.2.2]-octane-1,4-diyl, 1,3,4-thiadiazole-2,5-diyl, naphthalene-2,6-diyl, tetralin-2,6-diyl or decalin-2,6-diyl; $R^3$ and $R^4$ each independently are an alkyl or an alkenyl group, the alkyl and the alkenyl group being unsubstituted or substituted with at least one of halogen or cyano, in which optionally either 1 CH$_2$ group or 2 non-adjacent CH$_2$ groups is replaced by at least one of —O—, —COO— or —OOC—, or one of the groups of $R^3$ and $R^4$ is hydrogen, halogen, cyano or —NCS.

In spite of the high flexibility of the trimethylenoxy group $Z^1$, the compounds of formula I remarkably have a high tendency to form liquid crystalline phases, especially to form nematic, smectic A or tilted smectic (primarily $S_C$) phases in the case of the achiral compounds or to form cholesteric or chiral tilted smectic (primarily $S_C^*$) phases in the case of the chiral compounds. These mesophase types are especially suitable for the production of nematic, cholesteric or chiral tilted smectic phases in mixtures.

The compounds of formula I have a high stability, are comparatively simple to manufacture and have a very good solubility with one another and in known liquid crystal materials. Further, they have low viscosities and give short response times in indicating devices.

The compounds in accordance with the invention therefore facilitate a further optimization of liquid crystal mixtures and a modification of the electro-optical properties, for example, of the viscosities, of the elastic properties and the like.

The properties of the compounds of formula I can be varied in a wide range depending on the number and significance of the rings and depending on the choice of substituents. For example, aromatic rings lead to high values of the optical anisotropy and saturated rings lead to low values of the optical anisotropy, and a larger number of rings generally leads to higher clearing points. Polar end groups such as cyano, halogen or —NCS and rings such as pyrimidine-2,5-diyl, trans-1,3-dioxane-2,5-diyl etc. increase the dielectric anisotropy and lateral halogen or cyano substituents, pyridazine-2,5-diyl etc. reduce the dielectric anisotropy of the compounds of formula I. Further for example, the mesophase range and the solubility can be modified by lateral substitution of the rings and/or the elastic properties, the threshold potentials, the response times and the mesophases can be modified by a C—C double bond in the side-chain.

The above term "unsubstituted or methyl-, halogen- and/or cyano-substituted 1,4-phenylene, in which optionally 1–4 CH groups are replaced by nitrogen," embraces in the scope of the present invention groups such as 1,4-phenylene, pyridine-2,5-diyl, pyrazine-2,5-diyl, pyrimidine-2,5-diyl, pyridazine-3,6-diyl and tetrazine-3,6-diyl as well as rings which are substituted with methyl, halogen and/or cyano, especially methyl , halogen- and/or cyano-substituted 1,4-phenylene such as methyl-1,4-phenylene, fluoro-1,4-phenylene, 2,3-difluoro-1,4-phenylene, chloro-1,4-phenylene, cyano-1,4-phenylene, 2,3-dicyano-1,4-phenylene and the like.

The term "unsubstituted or methyl- and or cyano-substituted trans-1,4-cyclohexylene, in which optionally 2 CH$_2$ groups are replaced by oxygen and/or sulfur," embraces groups such as trans-1,4-cyclohexylene, trans-1,3-dioxane-2,5-diyl, trans-1,3-dithiane-2,5-diyl, 1-cyano-trans-1,4-cyclohexylene, 2-methyl-trans 1,4-cyclohexylene, 1-methyl-trans-1,4-cyclohexylene and the like.

The term "halogen" embraces fluorine, chlorine, bromine and iodine.

The term "alkyl" includes straight-chain and branched carbon groups including methyl, ethyl, propyl, butyl, pentyl, hexyl, heptyl, octyl, nonyl, decyl, undecyl, dodecyl and the like.

The term "alkenyl" includes straight-chain and branched carbon groups including vinyl, allyl, propenyl, butenyl, pentenyl, hexenyl, heptenyl, octenyl, nonenyl, decenyl, undecenyl, dodecenyl and the like.

The term "E" indicates a "trans"-substituted carbon-carbon double bond, and the term "Z" indicates a "cis"-substituted carbon-carbon double bond in line with conventional nomenclature. Similarly, the terms "E-isomer" and "Z-isomer" refer to the trans-isomer and to the cis-isomer, respectively, with respect to a double bond.

The term "unsubstituted or halogen- and/or cyano-substituted alkyl or alkenyl group, in which optionally 1 CH$_2$ group or 2 non-adjacent CH$_2$ groups is/are replaced by —O—, —COO— and/or —OOC—," embraces straight-chain and branched (optionally chiral) residues such as alkyl, 1-alkenyl (especially 1E-alkenyl), 3-alkenyl (especially 3E-alkenyl), 4-alkenyl (especially 4Z-alkenyl), 5-alkenyl, 6-alkenyl, 7-alkenyl and the like, residues derived therefrom which have ether and/or ester functions, such as alkoxy, alkoxymethoxy, alkenyloxy (for example, 2E-alkenyloxy, 3-alkenyloxy, 4-alkenyloxy, 5-alkenyloxy etc.), alkanoyloxy, alkenoyloxy, alkoxycarbonyl, alkenyloxycarbonyl, 1-(alkoxycarbonyl)ethoxy and the like and derived residues having halogen and/or cyano substituents such as 1-fluoroalkyl, 1-chloroalkyl, 1-cyanoalkyl, 1-fluoroalkoxy, 2-fluoroalkoxy, 1-chloroalkoxy, 2-chloroalkoxy, 1-cyanoalkoxy, 2-cyanoalkoxy, 2-fluoroalkanoyloxy, 2-chloroalkanoyloxy, 1-fluoroalkoxycarbonyl, 2-fluoroalkoxycarbonyl, 1-chloroalkoxycarbonyl, 2-chloroalkoxycarbonyl, 2-cyanoalkoxycarbonyl and the like. Examples of such residues are methyl, ethyl, propyl, butyl, pentyl, hexyl, heptyl, octyl, nonyl, decyl, undecyl, dodecyl, 1-methylheptyl, 2-methylbutyl, 3-methylpentyl, 4-methylhexyl, 5-methylheptyl, 6-methyloctyl, methoxy, ethoxy, propyloxy, butyloxy, pentyloxy, hexyloxy, heptyloxy, octyloxy, nonyloxy, decyloxy, undecyloxy, dodecyloxy, 1-methylheptyloxy, 2-methylbutyloxy, 3-methylpentyloxy, 4-methylhexyloxy, 5-methylheptyloxy, 6-methyloctyloxy, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, acetoxy, propanoyloxy, butanoyloxy, pentanoyloxy, hexanoyloxy, fluoroacetoxy, 2-fluoropropanoyloxy, 2-fluorobutanoyloxy, 2-fluoro- pentanoyloxy, 2-fluorohexanoyloxy, chloroacetoxy, 2-chloropropanoyloxy, 2-chlorobutanoyloxy, 2-chloro- pentanoyloxy, 2-chlorohexanoyloxy, 2-chloroheptanoyloxy, 1-methylheptyloxycarbonyl, 2-methylbutyloxycarbonyl, 2-methylpentyloxycarbonyl, 2-methylhexyloxycarbonyl, 2-fluoropropyloxycarbonyl, 2-fluorobutyloxycarbonyl, 2-fluoropentyloxycarbonyl, 2-fluorohexyloxycarbonyl, 2-fluoro-3-methylbutyloxycarbonyl, 2-fluoro-4-methyl-pentyloxycarbonyl, 2-chloropropyloxycarbonyl, 2-chlorobutyloxycarbonyl, 2-chloropentyloxycarbonyl, 2-chlorohexyloxycarbonyl, 2-chloro-3-methylbutyloxycarbonyl, 2-chloro-4-methylpentyloxycarbonyl, 2-cyanopropyloxycarbonyl, 2-cyanobutyloxycarbonyl, 2-cyanopentyloxy- carbonyl, 2-cyanohexyloxycarbonyl, 2-cyano-3-methylbutyloxycarbonyl, 2-cyano-4-methylpentyloxycarbonyl and the like.

The term "tetralin-2,6-diyl" denotes 1,2,3,4-tetrahydro-naphthalene-2,6-diyl. The term "decalin-2,6-diyl" embraces 2,6-disubstituted groups derived from decahydronaphthalene, especially (4aαH,8aβH)-decahydronaphthalen-2α,6β-yl.

The term "saturated ring" embraces unsubstituted or methyl- and/or cyano-substituted trans-1,4-cyclohexylene, in which optionally 2 $CH_2$ groups are replaced by oxygen and/or sulfur, as well as bicyclo[2,2,2]octane-1,4-diyl, decalin-2,6-diyl and, in connection with groups bonded in the 2-position, also tetralin-2,6-diyl. The term "aromatic ring" embraces unsubstituted or methyl-, halogen- and/or cyano-substituted 1,4-phenylene, in which optionally 1–4 CH groups are replaced by nitrogen, as well as 1,3,4-thiadiazole-2,5-diyl, naphthalene-2,6-diyl and, in connection with groups bonded in the 6-position, also tetralin-2,6-diyl.

In general there are preferred those compounds of formula I in which $A^1$, $A^2$, $A^3$, $A^4$ and $A^5$ each independently denote 1,4-phenylene or trans-1,4-cyclohexylene, or one of the groups $A^1$, $A^2$, $A^3$, $A^4$ and $A^5$ also denotes methyl-, halogen- and/or cyano-substituted 1,4-phenylene or methyl- and/or cyano-substituted trans-1,4-cyclohexylene, and/or one of the groups $A^1$, $A^2$, $A^3$, $A^4$ and $A^5$ also denotes 1,4-phenylene in which 1–4 (preferably 1 or 2) CH groups are replaced by nitrogen, trans-1,4-cylohexylene, in which 2 $CH_2$ groups are replaced by oxygen and/or sulfur, bicyclo[2,2,2]octane-1,4-diyl, 1,3,4-thiadiazole-2,5-diyl, naphthalene-2,6-diyl, tetralin-2,6-diyl or decalin-2,6-diyl. Further, there are preferred those compounds of formula I in which one of the groups $Z^2$, $Z^3$ and $Z^4$ (especially $Z^2$) is a single covalent bond, —$CH_2CH_2$—, —$CH_2O$—, —$OCH_2$—, —COO—, —OOC—, —$CH_2CH_2CH_2O$— or —$OCH_2CH_2CH_2$— and the other two of the groups $Z^2$, $Z^3$ and $Z^4$ each are a single covalent bond, —COO— and/or —OOC—.

Preferably, at least one of the groups $A^1$, $A^2$, $A^3$, $A^4$ and $A^5$ (especially at least one of the groups $A^1$ and $A^2$ bonded to $Z^1$) is a saturated ring, especially trans-1,4-cyclohexylene or trans-1,3-dioxane-2,5-diyl. These compounds generally have a higher tendency to form liquid crystalline phases. Preferably, the methylene group of the trimethylene group $Z^1$ is linked with a saturated ring (especially trans-1,4-cyclohexylene or trans-1,3-dioxane-2,5-diyl); that is, preferred compounds of formula I are those in which $Z^1$ is the group —$CH_2CH_2CH_2O$— and $A^1$ is a saturated ring or $Z^1$ is the group —$OCH_2CH_2CH_2$— and $A^2$ is a saturated ring, and especially those in which the saturated ring $A^1$ or $A^2$ is trans-1,4-cyclohexylene or trans-1,3-dioxane-2,5-diyl.

A preferred group of compounds in accordance with the invention comprises the compounds of the formula

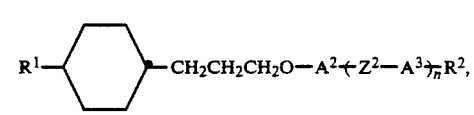

especially the compounds of the formulas

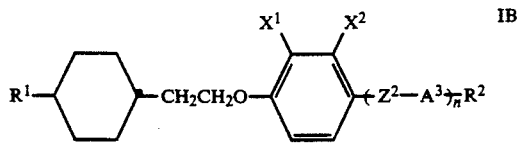

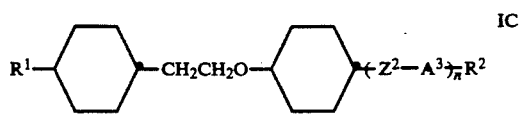

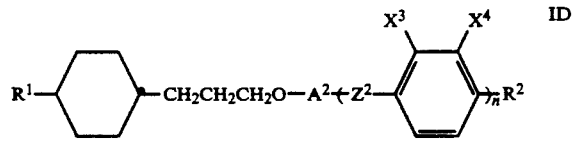

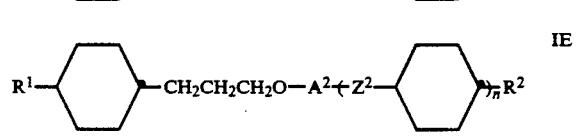

wherein in each case $A^2$, $A^3$, $R^1$, $R^2$, $Z^2$ and n each have the significances described above and $X^1$, $X^2$, $X^3$ and $X^4$ each independently denote hydrogen, methyl, halogen or cyano.

A further preferred group of compounds in accordance with the invention comprises the compounds of the formula

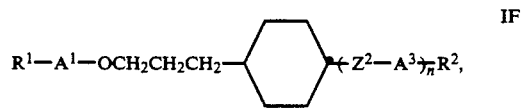

especially the compounds of the formula

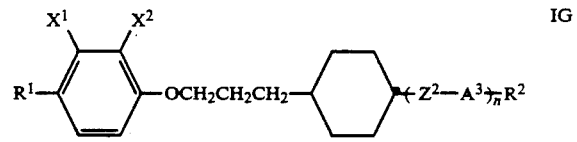

wherein $A^1$, $A^3$, $Z^2$, $R^1$, $R^2$ and n have the significances described above and $X^1$ and $X^2$ each independently are hydrogen, methyl, halogen or cyano.

The above remarks with respect to $A^2$, $A^3$, $A^4$, $A^5$, $Z^2$, $Z^3$ and $Z^4$ in formula I accordingly also apply to formulas IA–IG.

Examples of especially preferred sub-groups are the compounds of the formulas

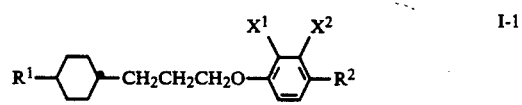

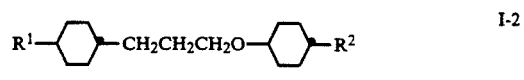

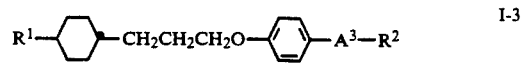

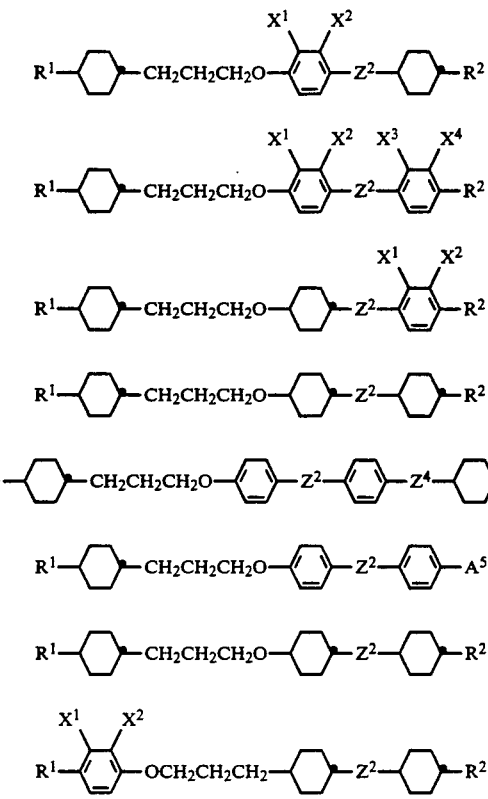

wherein $A^3$, $A^5$, $R^1$, $R^2$, $R^4$, $X^1$, $X^2$, $X^3$, $X^4$, $Z^2$ and $Z^4$ in each case have the significances described above. The compounds of formulas I and IA to IG in which n stands for the number 1 are for the most part liquid crystals having relatively high clearing points. Those compounds in which n stands for the number 0 are on the other hand primarily suitable as low-viscous doping substances, especially when $R^1$ is a group $R^3$ and $R^2$ is a group $R^4$.

The groups $A^1$, $A^2$, $A^3$, $A^4$ and $A^5$ in the above formulas I, IA to IG and I-1 to I-11 in each case preferably are 1,4-phenylene, fluoro-1,4-phenylene, 2,3-difluoro-1,4-phenylene, chloro-1,4-phenylene, cyano-1,4-phenylene, 2,3-dicyano-1,4-phenylene, methyl-1,4-phenylene, pyridine-2,5-diyl, pyazine-2,5-diyl, pyrimidine-2,5-diyl, trans-1,4-cyclohexylene, trans-1,3-dioxane-2,5-diyl, bicyclo[2,2,2]octane-1,4-diyl. 1,3,4-thiadiazole-2,5-diyl, naphthalene-2,6-diyl, tetralin-2,6-diyl or decalin-2,6-diyl, an optionally present group $A^4$ and/or $A^5$ preferably are 1,4-phenylene or trans-1,4-cyclohexylene. Especially preferred are in each case those compounds of the above formulas I, IA to IG and I-1 to I-11 in which one of the groups A (especially $A^3$ or $A^4$) present in the formula is 1,4-phenylene, fluoro-1,4-phenylene, 2,3-difluoro-1,4-phenylene, chloro-1,4-phenylene, cyano-1,4-phenylene, 2,3-dicyano-1,4-phenylene, methyl-1,4-phenylene or trans-1,4-cyclohexylene and/or one of the groups A (especially $A^2$ or $A^3$) present in the formula is 1,4-phenylene, pyridine-2,5-diyl, pyrazine-2,5-diyl, pyrimidine-2,5-diyl, trans-1,4-cyclohexylene, trans-1,3-dioxane-2,5-diyl, bicyclo[2,2,2]octane-1,4-diyl, 1,3,4-thiadiazole-2,5-diyl, naphthalene-2,6-diyl, tetralin-2,6-diyl or decalin-2,6-diyl and further groups A (especially also $A^4$ and $A^5$) optionally present in the formula each independently are 1,4-phenylene or trans-1,4-cyclohexylene.

In the above formulas I, IA to IG and I-1 to I-11 one of the groups $Z^2$, $Z^3$ and $Z^4$ preferably stands for a single covalent bond, —CH$_2$CH$_2$—, —CH$_2$O—, —OCH$_2$—, —COO—, —OOC—, —CH$_2$CH$_2$CH$_2$O— or —OCH$_2$CH$_2$CH$_2$— and the other two of the groups $Z^2$, $Z^3$ and $Z^4$ (or the other of the groups $Z^3$ and $Z^4$ in formulas I-1, I-2 and I-3 or the other of the groups $Z^2$ and $Z^3$ in formula I-9) preferably stand for single covalent bonds.

$X^1$, $X^2$, $X^3$ and $X^4$ in the above formulas IB, ID, IG, I-1, I-4, I-5, I-6 and I-11 preferably each individually are hydrogen, methyl, fluorine, chlorine and/or cyano, particularly hydrogen and/or fluorine. Preferably, a maximum of one or two of the substituents $X^1$-$X^4$ in the molecule have a significance different from hydrogen and, in particular, $X^1$-$X^4$ can also all are hydrogen.

Especially preferred significances of $A^3$ in formula I-3 are 1,4-phenylene, fluoro-1,4-phenylene, 2,3-difluoro-1,4-phenylene, pyridine-2,5-diyl, pyrimidine-2,5-diyl, trans-1,4-cyclohexylene, trans-1,3-dioxane-2,5-diyl and decalin-2,6-diyl.

In formula I-5 $Z^2$ preferably stands for a single covalent bond, —COO— or —OOC—. Further, there are in general preferred those compounds of formula I-5 in which one of the substituents $X^1$-$X^4$ (preferably $X^4$) is hydrogen, fluorine, chlorine, bromine or cyano, another of the substituents $X^1$-$X^4$ (preferably $X^3$) is hydrogen or fluorine and the other two of the substituents $X^1$-$X^4$ are hydrogen.

In formulas I-8 and I-9 $Z^2$ preferably stands for a single covalent bond, —COO— or —OOC—. Further, $A^5$ in formula I-9 can preferably are 1,4-phenylene, pyrimidine-2,5-diyl, trans-1,4-cyclohexylene or bicyclo-[2.2.2]-octane- 1,4-diyl.

In formulas I-10 and I-11 $Z^2$ preferably stands for a single covalent bond or —CH$_2$CH$_2$—. Hydrogen and fluorine are especially preferred significances of $X^1$ and $X^2$ in formula I-11.

In the above formulas I, IA to IG and I-1 to I-11 $R^1$ preferably is a group $R^3$ and $R^2$ preferably is a group $R^4$. Compounds in which R is a group $R^3$—$A^4$—$Z^3$— and/or $R^2$ is a group $R^4$—$A^5$—$Z^4$— are, however, likewise of interest, primarily as doping substances for increasing the clearing points of mixtures.

$R^3$ and $R^4$ preferably have a maximum of in each case about 18 carbon atoms, that is. $R^3$ and $R^4$ in the above formulas preferably each independently are an unsubstituted or halogen- and/or cyano-substituted $C_1$-$C_{18}$-alkyl or $C_2$—$C_{18}$-alkenyl group, in which optionally 1 CH$_2$ group or 2 non-adjacent CH$_2$ groups is/are replaced by —O—, —COO— and/or —OOC—, or one of the residues $R^3$ and $R^4$ can preferably also are hydrogen, halogen, cyano or —NCS. For nematic and cholesteric applications there are generally preferred short residues (for example, residues having a maximum of 12, preferably a maximum of 7, carbon atoms) and preferably one of the residues can also are hydrogen, halogen, cyano or —NCS. For smectic applications (especially tilted smectic phases) there are generally preferred those compounds in which $R^3$ and $R^4$ each independently are an unsubstituted or halogen- and/or cyano-substituted $C_1$-$C_{18}$-alkyl or $C_2$-$C_{18}$-alkenyl group, in which optionally 1 CH$_2$ group or 2 non-adjacent CH$_2$ groups is/are replaced by —O—, —COO— and/or —OOC—, and the sum of the carbon atoms in $R^3$ and $R^4$ together is at least 10, preferably at least 12.

Especially preferred residues $R^3$ are alkyl, alkenyl, alkoxy, alkenyloxy, alkoxycarbonyl, alkenyloxycarbonyl, alkanoyloxy and alkenoyloxy, especially alkyl, alkenyl, alkoxy and alkenyloxy. Especially preferred residues $R^4$ are alkyl, alkenyl, alkoxy, alkenyloxy, alkoxycarbonyl, alkenyloxycarbonyl, alkanoyloxy and alkenoyloxy, especially alkyl, alkenyl, alkoxy and alkenyloxy, as well as halogen (especially fluorine and chlorine), cyano and —NCS. Straight-chain residues $R^3$ or $R^4$ are generally preferred. In order to obtain, for example, chiral doping substances for cholesteric or for chiral tilted smectic liquid crystals, there can, however, also be used branched-chain residues and/or halogen- and/or cyano-substituted residues. In order to obtain a high spontaneous polarization in the case of smectic applications the centre of chirality (that is, the chain branching or the halogen or cyano substituent) should in this case preferably be close to the ring system, for example should be in the 1- or 2-position of the residue $R^3$ or $R^4$. Further, the tendency to form liquid crystalline phases fundamentally remains when one $CH_2$ group or 2 non-adjacent $CH_2$ groups in the chains is/are replaced by —O—, —COO— and/or —OOC—.

Further, the mesophase range, the threshold potential, the speed of response, the steepness of the transmission curve etc. can be varied by choosing the position of the C—C double bond in unsaturated residues such as alkenyl, alkenyloxy and the like. The effect is fundamentally known for example, from Mol. Cryst. Liq. Cryst. 122, 241 (1985), 131, 109 (1985) and 148, 123 (1987). There are preferred residues which have a double bond in the 1-position (especially E-isomer), in the 3-position (especially E-isomer) or in the 4-position (especially Z-isomer) of the chain with the inclusion of possible hetero atoms, such as 1E-alkenyl, 3E-alkenyl, 4Z-alkenyl, 2E-alkenyloxy, 3Z-alkenyloxy and the like. Further, the double bond can preferably also be in the terminal position, especially in the case of compounds for smectic applications. Examples of preferred residues having a double bond in the terminal position are 6-heptenyl, 7-octenyl, 8-nonenyl, 9-decenyl, 10-undecenyl, 11-dodecenyl, 5-hexenyloxy, 6-heptenyloxy, 7-octenyloxy, 8-nonenyloxy, 9-decenyloxy, 10-undecenyloxy, 11-dodecenyloxy and the like.

The manufacture of the compounds in accordance with the invention can be effected in a manner known per se from known compounds or analogues of known compounds. As a rule, the manufacture is effected most simply by etherifying the hydroxy compound in question with the corresponding 3-substituted 1-propyl halide (preferably the 1-propyl bromide). When one of the groups $Z^2$, $Z^3$ and $Z^4$ is —COO— or —OOC—, the manufacture can be effected preferably by esterifying the corresponding carboxylic acid with the corresponding hydroxy compound or by esterifying suitable derivatives thereof. Further, the compounds in which one of the rings is 1,3-dioxane or 1,3-dithiane can be obtained by reacting the corresponding aldehyde with the corresponding 2-substituted-1,3-propanediol or 1,3-propanedithiol.

The compounds in accordance with the invention can be used in the form of mixtures with one another and/or with other liquid crystal components. Suitable liquid crystal components are known to the person skilled in the art in large numbers, for example, from D. Demus et al., Flüssige Kristalle in Tabellen, VEB Deutscher Verlag für Grundstoffindustrie, Leipzig, Volumes I and II, and many of them are, moreover, commercially available.

The invention is therefore also concerned with a liquid crystalline mixture having at least 2 components, wherein at least one component is a compound of formula I (especially one of the compounds mentioned as being preferred).

Having regard to the good solubility and on the other hand to the large breadth of variation of the properties and fields of application, the amount of compounds of formula I in the mixtures in accordance with the invention can vary in a wide range and can amount to about 0.1 to 100 wt. %. For example, the mixture may include compounds of formula I. On the other hand for example, chiral doping substances are often used only in relatively small amounts for example, about 0.1 to 10 wt. %. In general, however, the amount of compounds of formula I in the mixtures in accordance with the invention amounts to about 1–60 wt. %. As a rule, a range of about 5–30 wt. % is preferred.

The mixtures in accordance with the invention for nematic or cholesteric applications preferably contain, in addition to one or more compounds of formula I, one or more compounds from the group of compounds of the formulas

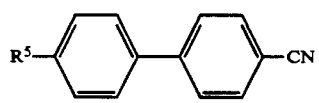

II

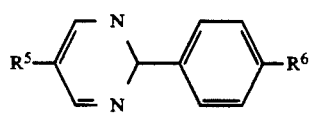

III

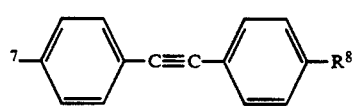

IV

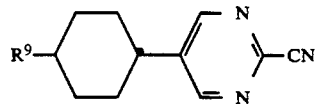

V

-continued
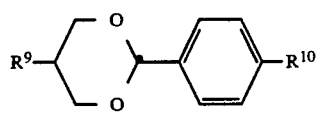  VI
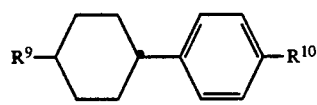  VII
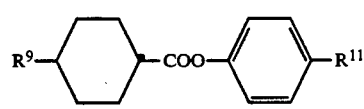  VIII
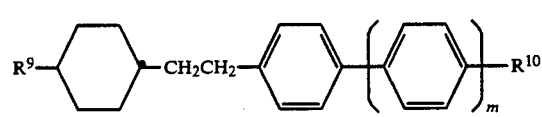  IX
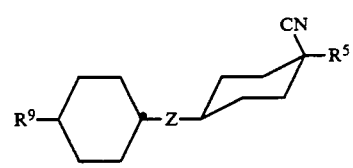  X
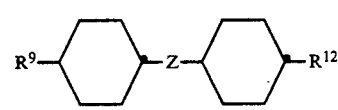  XI
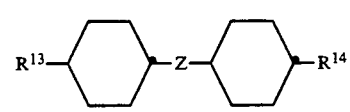  XII
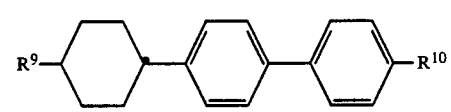  XIII
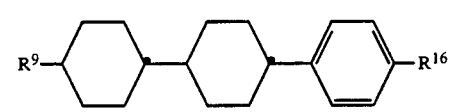  XIV
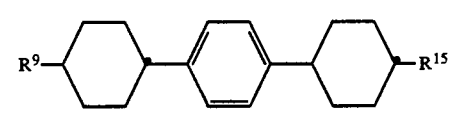  XV
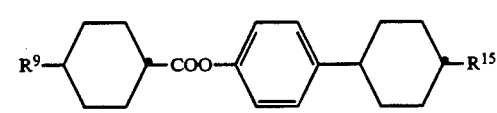  XVI
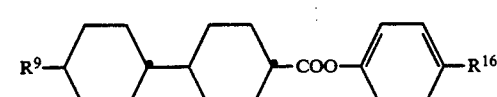  XVII
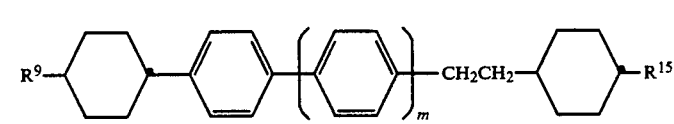  XVIII

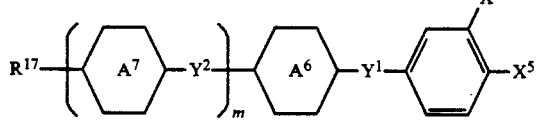

XIX wherein $R^5$ is alkyl, 3E-alkenyl or 4-alkenyl; $R^6$ represents cyano or fluorine; $R^7$ and $R^8$ denote alkyl or alkoxy: $R^9$ and $R^{15}$ each independently are alkyl, 1E-alkenyl, 3E-alkenyl or 4-alkenyl; $R^{10}$ denotes cyano, —NCS, alkyl, 1E-alkenyl, 3E-alkenyl, 4-alkenyl, alkoxy, 2E-alkenyloxy or 3-alkenyloxy; $R^{11}$ is alkoxy, 2E-alkenyloxy or 3-alkenyloxy; m stands for the number 0 or 1; Z represents a single covalent bond or —CH$_2$CH$_2$—; $R^{12}$ is cyano, alkyl, 1E-alkenyl, 3E-alkenyl or 4-alkenyl; $R^{13}$ denotes alkyl, 1E-alkenyl or 4-alkenyl; $R^{14}$ represents alkoxy, 2E-alkenyloxy or 3-alkenyloxy;

1,4-phenylene, in which optionally 1 CH group or 2 CH groups is/are replaced by nitrogen.

Preferably, the residues $R^5$ and $R^7$–$R^{17}$ have a maximum of in each case 12 carbon atoms, especially a maximum of in each case 7 carbon atoms.

The mixtures in accordance with the invention for smectic applications (especially for tilted smectic or chiral tilted smectic phases) preferably contain, in addition to one or more compounds of formula I, one or more compounds from the group of compounds of the formulas

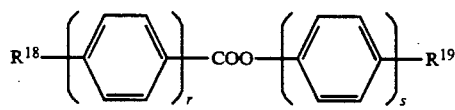

XX

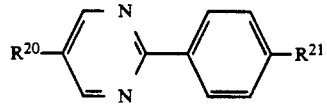

XXI

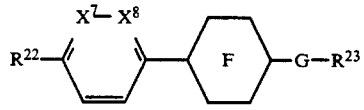

XXII

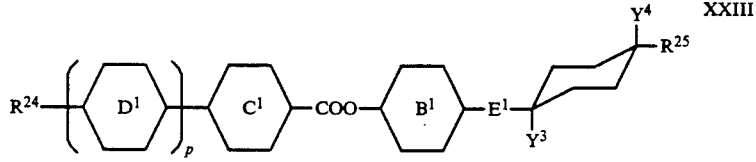

XXIII

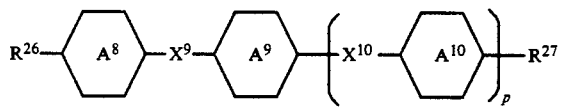

XXIV

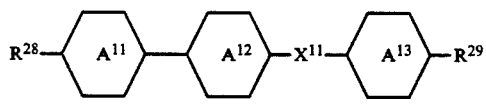

XXV

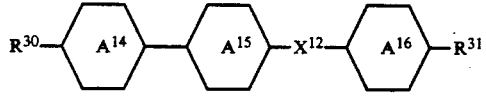

XXVI $R^{16}$ denotes cyano, alkyl, 1E-alkenyl, 3E-alkenyl, 4-alkenyl, alkoxy, 2E-alkenyloxy or 3-alkenyloxy; $X^5$ denotes fluorine or chlorine and $X^6$ denotes hydrogen, fluorine or chlorine; $R^{17}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and the rings $A^6$ and $A^7$ each independently represent trans-1,4-cyclohexylene, in which optionally 2 non-adjacent CH$_2$ groups are replaced by oxygen, or wherein $R^{18}$ and $R^{19}$ are alkyl, alkoxy, alkanoyl, alkanoyloxy, alkoxycarbonyl or alkoxycarbonyloxy with up to 18 carbon atoms; r and s each independently are 1 or 2; $R^{20}$ and $R^{21}$ represent alkyl or alkoxy with 1–18 carbon atoms; $X^7$ stands for CH and $X^8$ stands for N or $X^7$ stands for N and $X^8$ stands for CH; G is a single covalent bond, trans-1,4-cyclohexylene, cis-4-cyano-trans-1,4- cyclohexylene or 1,4-phenylene which is optionally substituted with halogen or methyl: ring F represents trans-1,4-cyclohexylene, 1,4-phenylene which is optionally substituted with halogen or methyl or, when G is a single covalent bond, ring F also represents cis-4-cyano-trans-1,4-cyclohexylene; $R^{22}$ and $R^{23}$ each denote an optionally halogen-substituted alkyl or alkenyl group, in which optionally one $CH_2$ group or two non-adjacent $CH_2$ groups is/are replaced by —O—, —COO— and/or —OOC—; p stands for the number 0 or 1; $E^1$ is a single covalent bond, —CH$_2$—CH$_2$—, —OCH$_2$—, —COO— or —OOC—; rings $B^1$, $C^1$ and $D^1$ denote 1,4-phenylene which is optionally substituted with cyano, halogen or lower alkyl; $Y^3$ and $Y^4$ are hydrogen or one of the substituents $Y^3$ and $Y^4$ also is cyano; $R^{24}$ and $R^{25}$ each individually represent optionally halogen-substituted $C_1$-$C_{18}$-alkyl or optionally halogen-substituted $C_2$-$C_{18}$-alkenyl, in which optionally one $CH_2$ group or two non-adjacent $CH_2$ groups is/are replaced by oxygen; $X^9$ represents a single covalent bond, —COO— or —OOC— and $X^{10}$ represents a single covalent bond, —COO—, —OOC—, —CH$_2$CH$_2$—, —OCH$_2$— or —CH$_2$O—; rings $A^8$, $A^9$ and $A^{10}$ each independently are unsubstituted or cyano-, halogen- or lower alkyl-substituted 1,4-phenylene or one of the rings also is pyrimidine-2,5-diyl or pyrazine-2,5-diyl and/or, when p stands for the number 1, one of the rings also is trans-1,4-cyclohexylene or trans-m-dioxane-2,5-diyl; $R^{26}$ is an optionally halogen-substituted alkenyl group with up to 18 carbon atoms, in which optionally 1 $CH_2$ group or 2 non-adjacent $CH_2$ groups is/are replaced by —O—, —CO—, —COO— or —OOC— and/or optionally a C—C single bond is replaced by a C—C double bond; $R^{27}$ is an optionally halogen substituted alkyl group with up to 18 carbon atoms, in which optionally 1 $CH_2$ group or 2 non- adjacent $CH_2$ groups is/are replaced by —O—, —CO—, —COO— or —OOC— and/or optionally a C—C single bond is replaced by a C—C double bond; $X^{11}$ denotes a single covalent bond, —COO—, —OOC—, —CH$_2$CH$_2$—, —OCH$_2$— or —CH$_2$O—; one of rings $A^{11}$, $A^{12}$ and $A^{13}$ represents pyrimidine-2,5-diyl, one of rings $A^{11}$, $A^{12}$ and $A^{13}$ represents unsubstituted or cyano-, halogen- or lower alkyl-substituted 1,4-phenylene and one of rings $A^{11}$, $A^{12}$ and $A^{13}$ represents trans- 1,4-cyclohexylene or unsubstituted or cyano-, halogen- or lower alkyl-substituted 1,4-phenylene; and $R^{28}$ and $R^{29}$ each independently are an optionally halogen-substituted alkyl group with up to 18 carbon atoms, in which optionally 1 $CH_2$ group or 2 non-adjacent $CH_2$ groups is/are replaced by —O—, —CO—, —COO— and/or —OOC—; $X^{12}$ denotes a single covalent bond, —COO—, —OOC—, —CH$_2$CH$_2$—, —OCH$_2$— or —CH$_2$O—; one of rings $A^{14}$, $A^{15}$ and $A^{16}$ represents trans m-dioxane 2,5-diyl and the other two of rings $A^{14}$, $A^{15}$ and $A^{16}$ each independently represent unsubstituted or cyano-, halogen- or lower alkyl-substituted 1,4-phenylene; and $R^{30}$ and $R^{31}$ each independently are an optionally halogen-substi- tuted alkyl group with up to 18 carbon atoms, in which optionally 1 $CH_2$ group or 2 non-adjacent $CH_2$ groups is/are replaced by —O—, —CO—, —COO— and/or —OOC—.

The manufacture of the liquid crystalline mixtures and of the electro-optical devices is carried out by methods known in the art.

The invention is illustrated in more detail by the following Examples. The optical antipodes of chiral compounds have in each case the same phase transition temperatures and the same absolute values for the twisting, but with opposite signs. The abbreviations used for the characterization of the phase transitions have the following significances:

C stands for crystalline
S stands for smectic
$S_A$, $S_B$, $S_C$ etc. stand for smectic A, B, C etc.
$S_C^*$, $S_F^*$ stand for chiral smectic C, F etc.
Ch stands for cholesteric
N stands for nematic
I stands for isotropic.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (°C.), normal pressure is about 1 atmosphere, and room temperature is about 23° C. Examples were carried out as written unless otherwise indicated.

EXAMPLE 1

A mixture of 0.5 g of 4-(5-nonyl-2-pyrimidinyl)-phenol, 0.55 g of 3-(trans-4-pentylcyclohexyl)-1-propyl bromide, 0.91 g of potassium carbonate and 50 ml of absolute butanone was heated under reflux overnight. Subsequently, the cooled reaction mixture was poured into water and extracted three times with 50 ml of diethyl ether each time. The combined organic phases were washed with 500 ml of water, dried over magnesium sulfate, filtered and concentrated. Chromatography of the residue on silica gel with toluene and recrystallization from ethanol gave pure 2-(4-[3-(trans-4-pentylcyclohexyl)-1-propyloxy]phenyl-5-nonylpyrimidine with m.p. (C—$S_C$) 83° C., transition $S_C$—N 103° C., cl.p. (N-I) 133° C.

The following compounds can be prepared in an analogous manner:
2-(4-[3-(trans-4-Methylcyclohexyl)-1-propyloxy]-phenyl)-5-propylpyrimidine;
2-(4-[3-(trans-4-ethylcyclohexyl)-1-propyloxy]phenyl)-5-propylpyrimidine;
2-(4-[3-(trans-4-propylcyclohexyl)-1-propyloxy]-phenyl)-5-propylpyrimidine;
20    2-(4-[3-(trans-4-butylcyclohexyl)-1-propyloxy]-phenyl)-5-propylpyrimidine;
2-(4-[3-(trans-4-pentylcyclohexyl)-1-propyloxy]-phenyl)-5-propylpyrimidine;
2-(4-[3-(trans-4-hexylcyclohexyl)-1-propyloxy]phenyl)-5-propylpyrimidine;
2-(4-[3-(trans-4-heptylcyclohexyl)-1-propyloxy]-phenyl)-5-propylpyrimidine;
2-(4-[3-(trans-4-octylcyclohexyl)-1-propyloxy]phenyl)-5-propylpyrimidine;
2-(4-[3-(trans-4-nonylcyclohexyl) 1-propyloxy]phenyl)-5-propylpyrimidine;
2-(4-[3-(trans-4-decylcyclohexyl)-1-propyloxy]phenyl)-5-propylpyrimidine;
2-(4-[3-(trans-4-methylcyclohexyl)-1-propyloxy]-phenyl)-5-butylpyrimidine;

2-(4-[3-(trans-4-ethylcyclohexyl)-1-propyloxy]phenyl)-5-butylpyrimidine;
2-(4-[3-(trans-4-propylcyclohexyl)-1-propyloxy]phenyl)-5-butylpyrimidine;
2-(4-[3-(trans-4-butylcyclohexyl)-1-propyloxy]phenyl)-5-butylpyrimidine;
2-(4-[3-(trans-4-pentylcyclohexyl)-1-propyloxy]phenyl)-5-butylpyrimidine;
2-(4-[3-(trans-4-hexylcyclohexyl)-1-propyloxy]phenyl)-5-butylpyrimidine;
2-(4-[3-(trans-4-heptylcyclohexyl)-1-propyloxy]phenyl)-5-butylpyrimidine;
2-(4-[3-(trans-4-octylcyclohexyl)-1-propyloxy]phenyl)-5-butylpyrimidine;
2-(4-[3-(trans-4-nonylcyclohexyl)-1-propyloxy]phenyl)-5-butylpyrimidine;
2-(4-[3-(trans-4-decylcyclohexyl)-1-propyloxy]phenyl)-5-butylpyrimidine;
2-(4-[3-(trans-4-methylcyclohexyl)-1-propyloxy]phenyl)-5-pentylpyrimidine;
2-(4-[3-(trans-4-ethylcyclohexyl)-1-propyloxy]phenyl)-5-pentylpyrimidine;
2-(4-[3-(trans-4-propylcyclohexyl)-1-propyloxy]phenyl)-5-pentylpyrimidine;
2-(4-[3-(trans-4-butylcyclohexyl)-1-propyloxy]phenyl)-5-pentylpyrimidine;
2-(4-[3-(trans-4-pentylcyclohexyl)-1-propyloxy]phenyl)-5-pentylpyrimidine, m.p. (C-N) 82° C., cl.p. (N-I) 139° C.;
2-(4-[3-(trans-4-hexylcyclohexyl)-1-propyloxy]phenyl)-5-pentylpyrimidine;
2-(4-[3-(trans-4-heptylcyclohexyl)-1-propyloxy]phenyl)-5-pentylpyrimidine;
2-(4-[3-(trans-4-octylcyclohexyl)-1-propyloxy]phenyl)-5-pentylpyrimidine;
2-(4-[3-(trans-4-nonylcyclohexyl)-1-propyloxy]phenyl)-5-pentylpyrimidine;
2-(4-[3-(trans-4-decylcyclohexyl)-1-propyloxy]phenyl)-5-pentylpyrimidine;
2-(4-[3-(trans-4-propylcyclohexyl)-1-propyloxy]phenyl)-5-hexylpyrimidine;
2-(4-[3-(trans-4-butylcyclohexyl)-1-propyloxy]phenyl)-5-hexylpyrimidine;
2-(4-[3-(trans-4-pentylcyclohexyl)-1-propyloxy]phenyl)-5-hexylpyrimidine, m.p. (C-N) 74° C.; cl.p. (N-I) 135° C.;
2-(4-[3-(trans-4-hexylcyclohexyl)-1-propyloxy]phenyl)-5-hexylpyrimidine;
2-(4-[3-(trans-4-heptylcyclohexyl)-1-propyloxy]phenyl)-5-hexylpyrimidine;
2-(4-[3-(trans-4-octylcyclohexyl)-1-propyloxy]phenyl)-5-hexylpyrimidine;
2-(4-[3-(trans-4-nonylcyclohexyl)-1-propyloxy]phenyl)-5-hexylpyrimidine;
2-(4-[3-(trans-4-decylcyclohexyl)-1-propyloxy]phenyl)-5-hexylpyrimidine;
2-(4-[3-(trans-4-methylcyclohexyl)-1-propyloxy]phenyl)-5-heptylpyrimidine;
2-(4-[3-(trans-4-ethylcyclohexyl)-1-propyloxy]phenyl)-5-heptylpyrimidine;
2-(4-[3-(trans 4-propylcyclohexyl)-1-propyloxy]phenyl)-5-heptylpyrimidine;
2-(4-[3-(trans-4-butylcyclohexyl)-1-propyloxy]phenyl)-5-heptylpyrimidine;
2-(4-[3-(trans-4-pentylcyclohexyl)-1-propyloxy]phenyl)-5-heptylpyrimidine, m.p. (C-N) 84° C., cl.p. (N-I) 137° C.;
2-(4-[3-(trans-4-hexylcyclohexyl)-1-propyloxy]phenyl)-5-heptylpyrimidine;
2-(4-[3-(trans-4-heptylcyclohexyl) 1-propyloxy]phenyl)-5-heptylpyrimidine;
2-(4-[3-(trans-4-octylcyclohexyl)-1-propyloxy]phenyl)-5-heptylpyrimidine;
2-(4-[3-(trans-4-nonylcyclohexyl)-1-propyloxy]phenyl)-5-heptylpyrimidine;
2-(4-[3-(trans-4-decylcyclohexyl)-1-propyloxy]phenyl)-5-heptylpyrimidine;
2-(4-[3-(trans-4-methylcyclohexyl)-1-propyloxy]phenyl)-5-octylpyrimidine;
2-(4-[3-(trans-4-ethylcyclohexyl)-1-propyloxy]phenyl)-5-octylpyrimidine;
2-(4-[3-(trans-4-propylcyclohexyl)-1-propyloxy]phenyl)-5-octylpyrimidine;
2-(4-[3-(trans-4-butylcyclohexyl)-1-propyloxy]phenyl)-5-octylpyrimidine;
2-(4-[3-(trans-4-pentylcyclohexyl)-1-propyloxy]phenyl)-5-octylpyrimidine, m.p. (C-$S_C$) 79° C. transition $S_C$-N 88° C., cl.p. (N-I) 133° C.;
2-(4-[3-(trans-4-hexylcyclohexyl)-1-propyloxy]phenyl)-5-octylpyrimidine;
2-(4-[3-(trans-4-heptylcyclohexyl)-1-propyloxy]phenyl)-5-octylpyrimidine;
2-(4-[3-(trans-4-octylcyclohexyl)-1-propyloxy]phenyl)-5-octylpyrimidine;
2-(4-[3-(trans-4-nonylcyclohexyl)-1-propyloxy]phenyl)-5-octylpyrimidine;
2-(4-[3-(trans-4-decylcyclohexyl)-1-propyloxy]phenyl)-5-octylpyrimidine;
2-(4-[3-(trans-4-methylcyclohexyl)-1-propyloxy]phenyl)-5-nonylpyrimidine;
2-(4-[3-(trans-4-ethylcyclohexyl)-1-propyloxy]phenyl)-5-nonylpyrimidine;
2-(4-[3-(trans-4-propylcyclohexyl)-1-propyloxy]phenyl)-5-nonylpyrimidine; 2-(4-[3-(trans 4-butylcyclohexyl)-1-propyloxy]phenyl)-5-nonylpyrimidine; 2-(4-[3-(trans-4-hexylcyclohexyl)-1-propyloxy]phenyl)-5-nonylpyrimidine; 2-(4-[3-(trans-4-heptylcyclohexyl)-1-propyloxy]phenyl)-5-nonylpyrimidine; 2-(4-[3-(trans-4-octylcyclohexyl)-1-propyloxy]phenyl)-5-nonylpyrimidine; 2-(4-[3-(trans-4-nonylcyclohexyl)-1-propyloxy]phenyl)-5-nonylpyrimidine;
2-(4-[3-(trans-4-decylcyclohexyl)-1-propyloxy]phenyl)-5-nonylpyrimidine;
2-(4-[3-(trans-4-methylcyclohexyl)-1-propyloxy]phenyl)-5-decylpyrimidine;
2-(4-[3-(trans-4-ethylcyclohexyl)-1-propyloxy]phenyl)-5-decylpyrimidine;
2-(4-[3-(trans-4-propylcyclohexyl)-1-propyloxy]phenyl)-5-decylpyrimidine;
2-(4-[3-(trans-4-butylcyclohexyl)-1-propyloxy]phenyl)-5-decylpyrimidine;
2-(4-[3-(trans-4-pentylcyclohexyl)-1-propyloxy]phenyl)-5-decylpyrimidine, m.p. (C-$S_C$) 69° C., transition $S_C$-N 110° C., cl.p. (N-I) 130° C.;
2-(4-[3-(trans-4-hexylcyclohexyl)-1-propyloxy])phenyl)-5-decylpyrimidine;
2-(4-[3-(trans-4-heptylcyclohexyl)-1-propyloxy])phenyl)-5-decylpyrimidine;
2-(4-[3-(trans-4-octylcyclohexyl)-1-propyloxy])phenyl)-5-decylpyrimidine;
2-(4-[3-(trans-4-nonylcyclohexyl)-1-propyloxy])phenyl)-5-decylpyrimidine;
2-(4-[3-(trans-4-decylcyclohexyl)-1-propyloxy])phenyl)-5-decylpyrimidine;

2-(4-[3-(trans-4-pentylcyclohexyl)-1-propyloxy]phenyl)-5-[(S)-2-methylbutyl]pyrimidine;
2-(4-[3-(trans-4-pentylcyclohexyl)-1-propyloxy]phenyl)-5-[(S)-3-methylpentyl]pyrimidine;
2-(4-[3-(trans-4-pentylcyclohexyl)-1-propyloxy]phenyl)-5-[(S)-4-methylhexyl]pyrimidine;
2-(4-[3-(trans-4-pentylcyclohexyl)-1-propyloxy]phenyl)-5-[(S)-5-methylheptyl]pyrimidine;
2-(4-[3-(trans-4-propylcyclohexyl)-1-propyloxy]phenyl)-5-methylpyridine;
2-(4-[3-(trans-4-propylcyclohexyl)-1-propyloxy]phenyl)-5-ethylpyridine;
2-(4-[3-(trans-4-propylcyclohexyl)-1-propyloxy]phenyl)-5-propylpyridine;
2-(4-[3-(trans-4-propylcyclohexyl)-1-propyloxy]phenyl)-5-butylpyridine;
2-(4-[3-(trans-4-propylcyclohexyl)-1-propyloxy]phenyl)-5-pentylpyridine;
2-(4-[3-(trans-4-propylcyclohexyl)-1-propyloxy]phenyl)-5-hexylpyridine;
2-(4-[3-(trans-4-propylcyclohexyl)-1-propyloxy]phenyl)-5-heptylpyridine;
2-(4-[3-(trans-4-propylcyclohexyl)-1-propyloxy]phenyl)-5-octylpyridine;
2-(4-[3-(trans-4-propylcyclohexyl)-1-propyloxy]phenyl)-5-nonylpyridine;
2-(4-[3-(trans-4-propylcyclohexyl)-1-propyloxy]phenyl)-5-decylpyridine;
2-(4-[3-(trans-4-pentylcyclohexyl) 1-propyloxy]phenyl)-5-methylpyridine;
2-(4-[3-(trans-4-pentylcyclohexyl)-1-propyloxy]phenyl)-5-ethylpyridine;
2-(4-[3-(trans-4-pentylcyclohexyl) 1-propyloxy]phenyl)-5-propylpyridine;
2-(4-[3-(trans-4-pentylcyclohexyl)-1-propyloxy]phenyl)-5-butylpyridine;
2-(4-[3-(trans-4-pentylcyclohexyl)-1-propyloxy]phenyl)-5-pentylpyridine;
2-(4-[3-(trans-4-pentylcyclohexyl)-1-propyloxy]phenyl)-5-hexylpyridine;
2-(4-[3-(trans-4-pentylcyclohexyl) 1-propyloxy]phenyl)-5-heptylpyridine;
2-(4-[3-(trans-4-pentylcyclohexyl)-1-propyloxy]phenyl)-5-octylpyridine;
2-(4-[3-(trans-4-pentylcyclohexyl)-1-propyloxy]phenyl)-5-nonylpyridine;
2-(4-[3-(trans-4-pentylcyclohexyl)-1-propyloxy]phenyl)-5-decylpyridine, m.p. (C-S) 57° C., transition S-S 71° C., transition S-S$_C$ 122° C. transition S$_C$-S$_A$ 136° C., cl.p. (S$_A$-I) 139° C.;
2-(4-[3-(trans-4-heptylcyclohexyl)-1-propyloxy]phenyl)-5-methylpyridine;
2-(4-[3-(trans-4-heptylcyclohexyl)-1-propyloxy]phenyl)- 5-ethylpyridine;
2-(4-[3-(trans-4-heptylcyclohexyl)-1-propyloxy]phenyl)-5-propylpyridine;
2-(4-[3-(trans-4-heptylcyclohexyl)-1-propyloxy]phenyl)-5-butylpyridine;
2-(4-[3-(trans-4-heptylcyclohexyl)-1-propyloxy]phenyl)-5-pentylpyridine:
2-(4-[3-(trans-4-heptylcyclohexyl)-1-propyloxy]phenyl)-5-hexylpyridine;
2-(4-[3-(trans-4-heptylcyclohexyl)-1-propyloxy]phenyl)-5-heptylpyridine;
2-(4-[3-(trans-4-heptylcyclohexyl)-1-propyloxy]phenyl)-5-octylpyridine;
2-(4-[3-(trans-4-heptylcyclohexyl)-1-propyloxy]phenyl)-5-nonylpyridine;
2-(4-[3-(trans-4-heptylcyclohexyl)-1-propyloxy]phenyl)-5-decylpyridine;
2-(4-[3-(trans-4-pentylcyclohexyl)-1-propyloxy]phenyl)-5-[(S)-2-methylbutyl]pyridine;
2-(4-[3-(trans-4-pentylcyclohexyl)-1-propyloxy]phenyl)-5-[(S)-3-methylpentyl]pyridine;
2-(4-[3-(trans-4-pentylcyclohexyl)-1-propyloxy]phenyl)-5-[(S)-4-methylhexyl]pyridine;
2-(4-[3-(trans-4-pentylcyclohexyl)-1-propyloxy]phenyl)-5-[(S)-5-methylheptyl]pyridine;
2-(4-[3-(trans-4-pentylcyclohexyl)-1-propyloxy]phenyl)-5-[(S)-6-methyloctyl]pyridine;
2-(4-[3-(trans-4-pentylcyclohexyl)-1-propyloxy]phenyl)-5-[(S)-1-methylheptyloxy]pyridine;
2-(4-[3-(trans-4-propylcyclohexyl)-1-propyloxy]phenyl)-5-methylpyrazine;
2-(4-[3-(trans-4-propylcyclohexyl)-1-propyloxy]phenyl)-5-ethylpyrazine;
2-(4-[3-(trans-4-propylcyclohexyl)-1-propyloxy]phenyl)-5-propylpyrazine;
2-(4-[3-(trans-4-propylcyclohexyl)-1-propyloxy]phenyl)-5-butylpyrazine;
2-(4-[3-(trans-4-propylcyclohexyl)-1-propyloxy]phenyl)-5-pentylpyrazine;
2-(4-[3-(trans-4-propylcyclohexyl)-1-propyloxy]phenyl)-5-hexylpyrazine;
2-(4-[3-(trans-4-propylcyclohexyl)-1-propyloxy]phenyl)-5-heptylpyrazine;
2-(4-[3-(trans-4-pentylcyclohexyl)-1-propyloxy]phenyl)-5-methylpyrazine;
2-(4-[3-(trans-4-pentylcyclohexyl)-1-propyloxy]phenyl)-5-ethylpyrazine;
2-(4-[3-(trans-4-pentylcyclohexyl)-1-propyloxy]phenyl)-5-propylpyrazine;
2-(4-[3-(trans-4-pentylcyclohexyl)-1-propyloxy]phenyl)-5-butylpyrazine;
2-(4-[3-(trans-4-pentylcyclohexyl)-1-propyloxy]phenyl)-5-pentylpyrazine;
2-(4-[3-(trans-4-pentylcyclohexyl)-1-propyloxy]phenyl)-5-hexylpyrazine;
2-(4-[3-(trans-4-pentylcyclohexyl)-1-propyloxy]phenyl)-5-heptylpyrazine;
2-(4-[3-(trans-4-heptylcyclohexyl)-1-propyloxy]phenyl)-5-methylpyrazine;
2-(4-[3-(trans- 4-heptylcyclohexyl)-1-propyloxy]phenyl)-5-ethylpyrazine;
2-(4-[3-(trans-4-heptylcyclohexyl)-1-propyloxy]phenyl)-5-propylpyrazine;
2-(4-[3-(trans-4-heptylcyclohexyl)-1-propyloxy]phenyl)-5-butylpyrazine;
2-(4-[3-(trans-4-heptylcyclohexyl)-1-propyloxy]phenyl)-5-pentylpyrazine; 2-(4-[3-(trans-4-heptylcyclohexyl)-1-propyloxy]phenyl)-5-hexylpyrazine;
2-(4-[3-(trans-4-heptylcyclohexyl)-1-propyloxy]phenyl)-5-heptylpyrazine;
2-methyl-5-(4-[3-(trans-4-pentylcyclohexyl)-1-propyloxy]phenyl)-1,3,4-thiadiazole;
2-ethyl-5-(4-[3-(trans-4-pentylcyclohexyl)-1-propyloxy]phenyl)-1.3.4-thiadiazole:
2-propyl-5-(4-[3-(trans-4-pentylcyclohexyl)-1-propyloxy]phenyl)-1,3,4-thiadiazole;
2-butyl-5-(4-[3-(trans-4-pentylcyclohexyl)-1-propyloxy]phenyl)-1,3,4-thiadiazole;
2-pentyl-5-(4-[3-(trans-4-pentylcyclohexyl)-1-propyloxy]phenyl)-1,3,4-thiadiazole;
2-hexyl-5-(4-[3-(trans-4-pentylcyclohexyl)-1-propyloxy]phenyl)-1,3,4-thiadiazole;

2-heptyl-5-(4-[3-(trans-4-pentylcyclohexyl)-1-propyloxy]phenyl)-1,3,4-thiadiazole;
2-octyl-5-(4-[3-(trans 4-pentylcyclohexyl)-1-propyloxy]phenyl)-1,3,4-thiadiazole;
2-nonyl-5-(4-[3-(trans-4-pentylcyclohexyl)-1-propyloxy]phenyl)-1,3,4-thiadiazole;
2-decyl-5-(4-[3-(trans-4-pentylcyclohexyl)-1-propyloxy]phenyl)-1,3,4-thiadiazole;
2-(4-methoxyphenyl)-5-[3-(trans-4-pentylcyclohexyl)-1-propyloxy]-1,3,4-thiadiazole;
2-(4-ethoxyphenyl)-5-[3-(trans-4-pentylcyclohexyl)-1-propyloxy]-1,3,4-thiadiazole;
2-(4-propyloxyphenyl)-5-[3-(trans-4-pentylcyclohexyl)-1-propyloxy]-1,3,4-thiadiazole;
2-(4-butoxyphenyl)-5-[3-(trans-4-pentylcyclohexyl)-1-propyloxy]-1,3,4-thiadiazole;
2-(4-pentyloxyphenyl)-5-[3-(trans-4-pentylcyclohexyl)-1-propyloxy]-1,3,4-thiadiazole;
2-(4-hexyloxyphenyl)-5-[3-(trans-4-pentylcyclohexyl)-1-propyloxy]-1,3,4-thiadiazole;
2-(4-heptyloxyphenyl)-5-[3-(trans-4-pentylcyclohexyl)-1-propyloxy]-1,3,4-thiadiazole;
2-(4-octyloxyphenyl)-5-[3-(trans-4-pentylcyclohexyl)-1-propyloxy]-1,3,4-thiadiazole;
2-(4-nonyloxyphenyl)-5-[3-(trans-4-pentylcyclohexyl)-1-propyloxy]-1,3,4-thiadiazole;
2-(4-decyloxyphenyl)-5-[3-(trans-4-pentylcyclohexyl)-1-propyloxy]-1,3,4-thiadiazole;
1-methoxy-4-[3-(trans-4-propylcyclohexyl) 1-propyloxy]benzene;
1-ethoxy-4-[3-(trans-4-propylcyclohexyl)-1-propyloxy]benzene;
1-propyloxy-4-[3-(trans-4-propylcyclohexyl)-1-propyloxy]benzene;
1-butyloxy-4-[3-(trans-4-propylcyclohexyl)-1-propyloxy]benzene;
1-pentyloxy-4-[3-(trans-4-propylcyclohexyl)-1-propyloxy]benzene;
1-hexyloxy-4-[3-(trans-4-propylcyclohexyl)-1-propyloxy]benzene;
1-heptyloxy-4-[3-(trans-4-propylcyclohexyl)-1-propyloxy]benzene;
1-octyloxy-4-[3-(trans-4-propylcyclohexyl) 1-propyloxy]benzene;
1-nonyloxy-4-[3-(trans-4-propylcyclohexyl)-1-propyloxy]benzene;
1-decyloxy-4-[3-(trans-4-propylcyclohexyl)-1-propyloxy]benzene;
1-methoxy-4-[3-(trans-4-pentylcyclohexyl)-1-propyloxy]benzene, m.p. (C-I) 47° C., cl.p. (N-I) 46° C.;
1-ethoxy-4-[3-(trans-4-pentylcyclohexyl)-1-propyloxy]benzene, m.p. (C-N) 50° C., cl.p. (N-I) 57° C.;
1-propyloxy-4-[3-(trans-4-pentylcyclohexyl)-1-propyloxy]benzene, m.p. (C-I) 51° C., cl.p. (N-I) 48° C.;
1-butyloxy-4-[3-(trans-4-pentylcyclohexyl)-1-propyloxy]benzene, m.p. (C-I) 59° C., transition S$_A$-N 45° C., cl.p. (N-I) 55° C.;
1-pentyloxy 4-[3-(trans-4-pentylcyclohexyl)-1-propyloxy]benzene, m.p. (C-S$_A$) 42° C., transition S$_A$-N 48° C. cl.p. (N-I) 53° C.;
1-hexyloxy-4-[3-(trans-4-pentylcyclohexyl)-1-propyloxy]benzene, m.p. (C-S$_A$) 44° C., transition S$_A$-N 54° C., cl.p. (N-I) 57° C.;
1-heptyloxy-4-[3-(trans-4-pentylcyclohexyl)-1-propyloxy]benzene, m.p. (C-S$_A$) 51° C., cl.p. (S$_A$-I) 57° C.;
1-octyloxy-4-[3-(trans-4-pentylcyclohexyl) 1-propyloxy]benzene;
1-nonyloxy-4-[3-(trans-4-pentylcyclohexyl)-1-propyloxy]benzene;
1-decyloxy-4-[3-(trans-4-pentylcyclohexyl)-1-propyloxy]benzene;
1-methoxy-4-[3-(trans-4-heptylcyclohexyl)-1-propyloxy]benzene;
1-ethoxy-4-[3-(trans-4-heptylcyclohexyl)-1-propyloxy]benzene;
1-propyloxy-4-[3-(trans-4-heptylcyclohexyl)-1-propyloxy]benzene;
1-butyloxy-4-[3-(trans-4-heptylcyclohexyl)-1-propyloxy]benzene;
1-pentyloxy-4-[3-(trans-4-heptylcyclohexyl)-1-propyloxy]benzene;
1-hexyloxy-4-[3-(trans-4-heptylcyclohexyl)-1-propyloxy]benzene;
1-heptyloxy-4-[3-(trans-4-heptylcyclohexyl)-1-propyloxy]benzene;
1-octyloxy-4-[3-(trans-4-heptylcyclohexyl)-1-propyloxy]benzene;
1-nonyloxy-4-[3-(trans 4-heptylcyclohexyl) 1-propyloxy]benzene;
1-decyloxy-4-[3-(trans-4-heptylcyclohexyl)-1-propyloxy]benzene;
1-[(R)-1-methylheptyloxy]-4-[3-(trans-4-[(S)-3-methylpentyl]cyclohexyl)-1-propyloxy]benzene;
1-methyl-4-[3-(trans-4-pentylcyclohexyl)-1-propyloxy]benzene;
1-ethyl-4-[3-(trans-4-pentylcyclohexyl)-1-propyloxy]benzene;
1-propyl-4-[3-(trans-4-pentylcyclohexyl)-1-propyloxy]benzene;
1-butyl-4-[3-(trans-4-pentylcyclohexyl)-1-propyloxy]benzene;
1-pentyl-4-[3-(trans-4-pentylcyclohexyl)-1-propyloxy]benzene;
1-hexyl-4-[3-(trans-4-pentylcyclohexyl)-1-propyloxy]benzene;
1-heptyl-4-[3-(trans-4-pentylcyclohexyl)-1-propyloxy]benzene;
1-octyl-4-[3-(trans-4-pentylcyclohexyl)-1-propyloxy]benzene;
1-nonyl-4-[3-(trans-4-pentylcyclohexyl)-1-propyloxy]benzene;
1-decyl-4-13-(trans-4-pentylcyclohexyl)-1-propyloxy]benzene;
4-[3-(trans-4-methylcyclohexyl)-1-propyloxy]benzonitrile;
4-[3-(trans-4-ethylcyclohexyl)-1-propyloxy]benzonitrile;
4-[3-(trans-4-propylcyclohexyl)-1-propyloxy]benzonitrile;
4-[3-(trans-4-butylcyclohexyl)-1-propyloxy]benzonitrile;
4-[3-(trans-4-pentylcyclohexyl)-1-propyloxy]benzonitrile, m.p. (C-I) 62° C., cl.p. (N-I) 54° C.;
4-[3-(trans-4-hexylcyclohexyl) 1-propyloxy]benzonitrile;
4-[3-(trans-4-heptylcyclohexyl)-1-propyloxy]benzonitrile;
4-[3-(trans-4-octylcyclohexyl)-1-propyloxy]benzonitrile;
4-[3-(trans-4-nonylcyclohexyl)-1-propyloxy]benzonitrile;
4-[3-(trans-4-decylcyclohexyl)-1-propyloxy]benzonitrile;

4-[3-(trans-4-methylcyclohexyl)-1-propyloxy]-2-fluorobenzonitrile;
4-[3-(trans-4-ethylcyclohexyl)-1-propyloxy]-2-fluorobenzonitrile;
4-[3-(trans-4-propylcyclohexyl)-1-propyloxy]-2-fluorobenzonitrile;
4-[3-(trans-4-butylcyclohexyl)-1-propyloxy]-2-fluorobenzonitrile;
4-[3-(trans-4-pentylcyclohexyl)-1-propyloxy]-2-fluorobenzonitrile, m.p. (C-I) 59° C., cl.p. (N-I) 29° C.;
4-[3-(trans-4-hexylcyclohexyl)-1-propyloxy]-2-fluorobenzonitrile;
4-[3-(trans-4-heptylcyclohexyl)-1-propyloxy]-2-fluorobenzonitrile;
4-[3-(trans-4-octylcyclohexyl)-1-propyloxy]-2-fluorobenzonitrile;
4-[3-(trans-4-nonylcyclohexyl)-1-propyloxy]-2-fluorobenzonitrile;
4-[3-(trans-4-decylcyclohexyl)-1-propyloxy]-2-fluorobenzonitrile;
4-[3-(trans-4-methylcyclohexyl)-1-propyloxy]-3-fluorobenzonitrile;
4-[3-(trans-4-ethylcyclohexyl)-1-propyloxy]-3-fluorobenzonitrile;
4-[3-(trans-4-propylcyclohexyl)-1-propyloxy]-3-fluorobenzonitrile;
4-[3-(trans-4-butylcyclohexyl)-1-propyloxy]-3-fluorobenzonitrile;
4-[3-(trans-4-pentylcyclohexyl)-1-propyloxy]-3-fluorobenzonitrile, m.p. (C-N) 45° C., cl.p. (N-I) 46° C.;
4-[3-(trans-4-hexylcyclohexyl)-1-propyloxy]-3-fluorobenzonitrile;
4-[3-(trans-4-heptylcyclohexyl)-1-propyloxy]-3-fluorobenzonitrile;
4-[3-(trans-4-octylcyclohexyl)-1-propyloxy]-3-fluorobenzonitrile;
4-[3-(trans-4-nonylcyclohexyl)-1-propyloxy]-3-fluorobenzonitrile;
4-[3-(trans-4-decylcyclohexyl)-1-propyloxy]-3-fluorobenzonitrile;
1-[3-(trans-4-methylcyclohexyl)-1-propyloxy]-4-fluorobenzene;
1-[3-(trans-4-ethylcyclohexyl)-1-propyloxy]-4-fluorobenzene;
1-[3-(trans-4-propylcyclohexyl)-1-propyloxy]-4-fluorobenzene;
1-[3-(trans-4-butylcyclohexyl)-1-propyloxy]-4-fluorobenzene;
1-[3-(trans-4-pentylcyclohexyl)-1-propyloxy]-4-fluorobenzene; m.p. (C-I) 17° C., cl.p. (N-I) 11° C.;
1-[3-(trans-4-hexylcyclohexyl)-1-propyloxy]-4-fluorobenzene;
1-[3-(trans-4-heptylcyclohexyl)-1-propyloxy]-4-fluorobenzene;
1-[3-(trans-4-pentylcyclohexyl)-1-propyloxy]-4-chlorobenzene, m.p. (C-I) 37° C., cl.p. (N-I) 33° C.;
1-[3-(trans-4-pentylcyclohexyl)-1-propyloxy]-4-bromobenzene, m.p. (C-I) 48° C., cl.p. (N-I) 37° C.;
1-[3-(trans-4-pentylcyclohexyl)-1-propyloxy]-4-iodobenzene, m.p. (C-I) 54° C., cl.p. (N-I) 34° C.;
1-[3-(trans-4-methylcyclohexyl)-1-propyloxy]-3,4-difluorobenzene;
1-[3-(trans-4-ethylcyclohexyl)-1-propyloxy]-3,4-difluorobenzene;
1-[3-(trans-4-propylcyclohexyl)-1-propyloxy]-3,4-difluorobenzene;
1-[3-(trans-4-butylcyclohexyl)-1-propyloxy]-3,4-difluorobenzene;
1-[3-(trans-4-pentylcyclohexyl)-1-propyloxy]-3,4-difluorobenzene, m.p. (C-I) 4° C.;
1-[3-(trans-4-hexylcyclohexyl)-1-propyloxy]-3,4-difluorobenzene;
1-[3-(trans-4-heptylcyclohexyl)-1-propyloxy]-3,4-difluorobenzene;
1-[3-(trans-4-octylcyclohexyl)-1-propyloxy]-3,4-difluorobenzene;
1-[3-(trans-4-[trans-4-propylcyclohexyl]cyclohexyl)-1-propyloxy]-4-fluorobenzene;
1-[3-(trans-4-[trans-4-pentylcyclohexyl]cyclohexyl)-1-propyloxy]-4-fluorobenzene, m.p. (C-$S_B$) 69° C., transition $S_B$-N 95° C., cl.p. (N-I) 127° C.;
1-[3-(trans-4-[trans-4-propylcyclohexyl]cyclohexyl)-1-propyloxy]-3,4-difluorobenzene, m.p (C-N) 79° C., cl.p. (N-I) 107° C.;
1-[3-(trans-4-[trans-4-pentylcyclohexyl]cyclohexyl)-1-propyloxy]-3,4-difluorobenzene, m.p. (C-$S_B$) 57° C., transition $S_B$-N 81° C., cl.p. (N-I) 112° C.;
4-[3-(trans-4-[trans-4-propylcyclohexyl]cyclohexyl)-1-propyloxy]-3-fluorobenzonitrile;
4-[3-(trans-4-[trans-4-pentylcyclohexyl]cyclohexyl)-1-propyloxy]-3-fluorobenzonitrile, m.p. (C-N) 98° C., cl.p. (N-1) 143° C.;
4-[3-(trans-4-[trans-4-propylcyclohexyl]cyclohexyl)-1-propyloxy]benzonitrile;
4-[3-(trans-4-[trans-4-pentylcyclohexyl]cyclohexyl)-1-propyloxy]benzonitrile, m.p. (C-N) 93° C., cl.p. (N-I) 159° C.;
1-[3-(trans-4-[trans-4-propylcyclohexyl]cyclohexyl)-1-propyloxy-4-ethoxy-2,3-difluorobenzene, m.p. (C-N) 59° C., cl.p. (N-I) 136° C.;
1-[3-(trans-4-[trans-4-pentylcyclohexyl]cyclohexyl) 1-propyloxy]-4-ethoxy-2,3-difluorobenzene, m.p. (C-$S_A$) 49° C., transition $S_A$-N 100° C., cl.p. (N-I) 137° C.;
4-[3-(trans-4-methylcyclohexyl)-1-propyloxy]-phenylisothiocyanate;
4-[3-(trans-4-ethylcyclohexyl)-1-propyloxy]-phenylisothiocyanate;
4-[3-(trans-4-propylcyclohexyl)-1-propyloxy]-phenylisothiocyanate;
4-[3-(trans-4-butylcyclohexyl)-1-propyloxy]-phenylisothiocyanate;
4-[3-(trans-4-pentylcyclohexyl)-1-propyloxy]-phenylisothiocyanate;
4-[3-(trans-4-hexylcyclohexyl)-1-propyloxy]-phenylisothiocyanate;
4-[3-(trans-4-heptylcyclohexyl)-1-propyloxy]-phenylisothiocyanate;
4-[3-(trans-4-octylcyclohexyl)-1-propyloxy]-phenylisothiocyanate;
2,3-dicyano-1-propyl-4-[3-(trans-4-propylcyclohexyl)-1-propyloxy]benzene;
2,3-dicyano-1-pentyl-4-[3-(trans-4-propylcyclohexyl)-1-propyloxy]benzene;
2,3-dicyano-1-heptyl-4-[3-(trans-4-propylcyclohexyl)-1-propyloxy]benzene;
2,3-dicyano-1-propyl-4-[3-(trans-4-pentylcyclohexyl)-1-propyloxy]benzene;
2,3-dicyano-1-pentyl-4-[3-(trans-4-pentylcyclohexyl)-1-propyloxy]benzene, m.p. (C-I) 123° C.;
2,3-dicyano-1-heptyl-4-[3-(trans-4-pentylcyclohexyl)-1-propyloxy]benzene;
2,3-dicyano-1-propyl-4-[3-(trans-4-heptylcyclohexyl)-1-propyloxy]benzene;

2,3-dicyano-1-pentyl-4-[3-(trans-4-heptylcyclohexyl)-1-propyloxy]benzene;
2,3-dicyano-1-heptyl-4-[3-(trans-4-heptylcyclohexyl)-1-propyloxy]benzene;
2,3-difluoro-1-ethoxy-4-[3-(trans-4-propylcyclohexyl)-1-propyloxy]benzene;
2,3-difluoro-1-ethoxy-4-[3-(trans-4-pentylcyclohexyl)-1-propyloxy]benzene;
2,3-dicyano-1-[3-(trans-4-propylcyclohexyl)-1 propyloxy]-4-[2-(trans-4-pentylcyclohexyl)ethyl]benzene;
2,3-dicyano-1-[3-(trans-4-pentylcyclohexyl)-1-propyloxy]-4-[2-(trans-4-pentylcyclohexyl)ethyl]benzene, m.p. (C-I) 198° C.;
2,3-dicyano-1-[3-(trans-4-heptylcyclohexyl)-1-propyloxy]-4-[2-(trans-4-pentylcyclohexyl)ethyl]benzene;
4-[3-(trans-4-methylcyclohexyl)-1-propyloxy]-4'-cyanobiphenyl;
4-[3-(trans-4-ethylcyclohexyl)-1-propyloxy]-4'-cyanobiphenyl;
4-[3-(trans-4-propylcyclohexyl)-1-propyloxy]-4'-cyanobiphenyl;
4-[3-(trans-4-butylcyclohexyl)-1-propyloxy]-4'-cyanobiphenyl;
4-[3-(trans-4-pentylcyclohexyl)-1-propyloxy]-4'-cyanobiphenyl, m.p. (C-S$_A$) 83° C., transition S$_A$-N 149° C., cl.p. (N-I) 167° C.;
4-[3-(trans-4-hexylcyclohexyl)-1-propyloxy]-4'-cyanobiphenyl;
4-[3-(trans-4-heptylcyclohexyl)-1-propyloxy]-4'-cyanobiphenyl;
4-[3-(trans-4-octylcyclohexyl)-1-propyloxy]-4'-cyanobiphenyl;
4-[3-(trans-4-methylcyclohexyl)-1-propyloxy]-4'-fluorobiphenyl;
4-[3-(trans-4-ethylcyclohexyl)-1-propyloxy]-4'-fluorobiphenyl;
4-[3-(trans-4-propylcyclohexyl)-1-propyloxy]-4'-fluorobiphenyl;
4-[3-(trans-4-butylcyclohexyl)-1-propyloxy]-4'-fluorobiphenyl;
4-[3-(trans-4-pentylcyclohexyl)-1-propyloxy]-4'-fluorobiphenyl;
4-[3-(trans-4-hexylcyclohexyl)-1-propyloxy]-4'-fluorobiphenyl;
4-[3-(trans-4-heptylcyclohexyl)-1-propyloxy]-4'-fluorobiphenyl;
4-[3-(trans-4-octylcyclohexyl) 1-propyloxy]-4'-fluorobiphenyl;
(R)-α-[(4'-[3-(trans-4-pentylcyclohexyl)-1-propyloxy]-4-biphenylyl)oxy]propionic acid ethyl ester, m.p. (C-S$_A$) 79° C. transition S$_A$-Ch 80° C., cl.p. (Ch-I) 81° C.;
1,4-di-[3-(trans-4-methylcyclohexyl)-1-propyloxy]benzene;
1,4-di-[3-(trans-4-ethylcyclohexyl)-1-propyloxy]benzene;
1,4-di-[3-(trans-4-propylcyclohexyl)-1-propyloxy]benzene;
1,4-di-[3-(trans-4-butylcyclohexyl)-1-propyloxy]benzene;
1,4-di-[3-(trans-4-pentylcyclohexyl)-1-propyloxy]benzene, m.p. (C-S$_A$) 108° C., transition S$_A$-N 112° C., N-I 115° C.;
1,4-di-[3-(trans-4-hexylcyclohexyl)-1-propyloxy]benzene;
1,4-di-[3-(trans-4-heptylcyclohexyl)-1-propyloxy]benzene;
1,4-di-[3-(trans-4-octylcyclohexyl)-1-propyloxy]benzene;
1,4-di-[3-(trans-4-nonylcyclohexyl)-1-propyloxy]benzene;
1,4-di-[3-(trans-4-decylcyclohexyl)-1-propyloxy]benzene; 1-[3-(trans-4-pentylcyclohexyl)-1-propyloxy]-4-[3-(trans-4-propylcyclohexyl)-1-propyloxy]benzene;
4,4'-di-[3-(trans-4-methylcyclohexyl)-1-propyloxy]biphenyl;
4,4'-di-[3-(trans-4-ethylcyclohexyl)-1-propyloxy]biphenyl;
4,4'-di-[3-(trans-4-propylcyclohexyl)-1-propyloxy]biphenyl;
4,4'-di-[3-(trans 4-butylcyclohexyl)-1-propyloxy]biphenyl;
4,4'-di-[3-(trans-4-pentylcyclohexyl)-1-propyloxy]biphenyl, m.p. (C-S) 67° C., transition S-S$_A$ 182° C., cl.p. (S$_A$-I) 202° C.:
4,4'-di-[3-(trans-4-hexylcyclohexyl)-1-propyloxy]biphenyl;
4,4'-di-[3-(trans-4-heptylcyclohexyl)-1-propyloxy]biphenyl;
4,4'-di-[3-(trans-4-octylcyclohexyl)-1-propyloxy]biphenyl;
4,4'-di-[3-(trans-4-nonylcyclohexyl)-1-propyloxy]biphenyl;
4,4'-di-[3-(trans-4-decylcyclohexyl)-1-propyloxy]biphenyl;
4-[3-(trans-4-pentylcyclohexyl)-1-propyloxy]-4'-[3-trans-4-propylcyclohexyl)-1-propyloxy]biphenyl;
1-[3-(trans-4-methylcyclohexyl)-1-propyloxy]-4-[2-(trans-4-methylcyclohexyl)ethyl]benzene;
1-[3-(trans-4-ethylcyclohexyl)-1-propyloxy]-4-[2-(trans-4-methylcyclohexyl)ethyl]benzene;
1-[3-(trans-4-propylcyclohexyl)-1-propyloxy]-4-[2-(trans-4-methylcyclohexyl)ethyl]benzene;
1-[3-(trans-4-butylcyclohexyl)-1-propyloxy]-4-[2-(trans-4-methylcyclohexyl)ethyl]benzene;
1-[3-(trans-4-pentylcyclohexyl)-1-propyloxy]-4-[2-(trans-4-methylcyclohexyl)ethyl]benzene;
1-[3-(trans-4-hexylcyclohexyl)-1-propyloxy]-4-[2-(trans-4-methylcyclohexyl)ethyl]benzene;
1-[3-(trans-4-heptylcyclohexyl)-1-propyloxy]-4-[2-(trans-4-methylcyclohexyl)ethyl]benzene;
1-[3-(trans-4-methylcyclohexyl)-1-propyloxy]-4-[2-(trans-4-ethylcyclohexyl)ethyl]benzene;
1-[3-(trans-4-ethylcyclohexyl)-1-propyloxy]-4-[2-(trans-4-ethylcyclohexyl)ethyl]benzene;
1-[3-(trans-4-propylcyclohexyl)-1-propyloxy]-4-[2-(trans-4-ethylcyclohexyl)ethyl]benzene;
1-[3-(trans-4-butylcyclohexyl)-1-propyloxy]-4-[2-(trans-4-ethylcyclohexyl)ethyl]benzene;
1-[3-(trans-4-pentylcyclohexyl)-1-propyloxy]-4-[2-(trans-4-ethylcyclohexyl)ethyl]benzene;
1-[3-(trans-4-hexylcyclohexyl)-1-propyloxy]-4-[2-(trans-4-ethylcyclohexyl)ethyl]benzene;
1-[3-(trans-4-heptylcyclohexyl)-1-propyloxy]-4-[2-(trans-4-ethylcyclohexyl)ethyl]benzene;
1-[3-(trans-4-methylcyclohexyl)-1-propyloxy]-4-[2-(trans-4-propylcyclohexyl)ethyl]benzene;
1-[3-(trans-4-ethylcyclohexyl)-1-propyloxy]-4-[2-(trans-4-propylcyclohexyl)ethyl]benzene;
1-[3-(trans-4-propylcyclohexyl)-1-propyloxy]-4-[2-(trans-4-propylcyclohexyl)ethyl]benzene;
1-[3-(trans-4-butylcyclohexyl)-1-propyloxy]-4-[2-(trans-4-propylcyclohexyl)ethyl]benzene;
1-[3-(trans-4-pentylcyclohexyl)-1-propyloxy]-4-[2-(trans-4-propylcyclohexyl)ethyl]benzene;

1-[3-(trans-4-hexylcyclohexyl)-1-propyloxy]-4-[2-(trans-4-propylcyclohexyl)ethyl]benzene;
1-[3-(trans-4-heptylcyclohexyl)-1-propyloxy]-4-[2-(trans-4-propylcyclohexyl)ethyl]benzene;
1-[3-(trans-4-methylcyclohexyl)-1-propyloxy]-4-[2-(trans-4-butylcyclohexyl)ethyl]benzene;
1-[3-(trans-4-ethylcyclohexyl)-1-propyloxy]-4-[2-(trans-4-butylcyclohexyl)ethyl]benzene;
1-[3-(trans-4-propylcyclohexyl)-1-propyloxy]-4-[2-(trans-4-butylcyclohexyl)ethyl]benzene;
1-[3-(trans-4-butylcyclohexyl)-1-propyloxy]-4-[2-(trans-4-butylcyclohexyl)ethyl]benzene;
1-[3-(trans-4-pentylcyclohexyl)-1-propyloxy]-4-[2-(trans-4-butylcyclohexyl)ethyl]benzene;
1-[3-(trans-4-hexylcyclohexyl)-1-propyloxy]-4-[2-(trans-4-butylcyclohexyl)ethyl]benzene;
1-[3-(trans-4-methylcyclohexyl)-1-propyloxy]-4-[2-(trans-4-butylcyclohexyl)ethyl]benzene;
1-[3-(trans-4-methylcyclohexyl)-1-propyloxy]-4-[2-(trans-4-pentylcyclohexyl)ethyl]benzene;
1-[3-(trans-4-ethylcyclohexyl)-1-propyloxy]-4-[2-(trans-4-pentylcyclohexyl)ethyl]benzene;
1-[3-(trans-4-propylcyclohexyl)-1-propyloxy]-4-[2-(trans-4-pentylcyclohexyl)ethyl]benzene;
1-[3-(trans-4-butylcyclohexyl)-1-propyloxy]-4-[2-(trans-4-pentylcyclohexyl)ethyl]benzene;
1-[3-(trans-4-pentylcyclohexyl)-1-propyloxy]-4-[2-(trans-4-pentylcyclohexyl)ethyl]benzene, m.p. (C-S$_B$) 86° C., transition S$_B$-N 109° C., cl.p. (N-I) 117° C.;
1-[3-(trans-4-hexylcyclohexyl)-1-propyloxy]-4-[2-(trans-4-pentylcyclohexyl)ethyl]benzene;
1-[3-(trans-4-heptylcyclohexyl)-1-propyloxy]-4-[2-(trans-4-pentylcyclohexyl)ethyl]benzene;
1-[3-(trans-4-methylcyclohexyl)-1-propyloxy]-4-[2--(trans-4-hexylcyclohexyl)ethyl]benzene;
1-[3-(trans-4-ethylcyclohexyl)-1-propyloxy]-4-[2-(trans-4-hexylcyclohexyl)ethyl]benzene;
1-[3-(trans-4-propylcyclohexyl)-1-propyloxy]-4-[2-(trans-4-hexylcyclohexyl)ethyl]benzene;
1-[3-(trans-4-butylcyclohexyl)-1-propyloxy]-4-[2-(trans-4-hexylcyclohexyl)ethyl]benzene;
1-[3-(trans-4-pentylcyclohexyl)-1-propyloxy]-4-[2-(trans-4-hexylcyclohexyl)ethyl]benzene;
1-[3-(trans-4-hexylcyclohexyl)-1-propyloxy]-4-[2-(trans-4-hexylcyclohexyl)ethyl]benzene;
1-[3-(trans-4-heptylcyclohexyl)-1-propyloxy]-4-[2-(trans-4-hexylcyclohexyl)ethyl]benzene;
1-[3-(trans-4-methylcyclohexyl)-1-propyloxy]-4-[2-(trans-4-heptylcyclohexyl)ethyl]benzene;
1-[3-(trans-4-ethylcyclohexyl)-1-propyloxy]-4-[2-(trans-4-heptylcyclohexyl)ethyl]benzene;
1-[3-(trans-4-propylcyclohexyl)-1-propyloxy]-4-[2-(trans-4-heptylcyclohexyl)ethyl]benzene;
1-[3-(trans-4-butylcyclohexyl)-1-propyloxy]-4-[2-(trans-4-heptylcyclohexyl)ethyl]benzene;
1-[3-(trans-4-pentylcyclohexyl)-1-propyloxy]-4-[2-(trans-4-heptylcyclohexyl)ethyl]benzene;
1-[3-(trans-4-hexylcyclohexyl)-1-propyloxy]-4-[2-(trans-4-heptylcyclohexyl)ethyl]benzene;
1-[3-(trans-4-heptylcyclohexyl)-1-propyloxy]-4-[2-(trans-4-heptylcyclohexyl)ethyl]benzene;
4-[3-(trans-4-propylcyclohexyl)-1-propyloxy]-4'-[2-(trans-4-propylcyclohexyl)ethyl]biphenyl;
4-[3-(trans-4-pentylcyclohexyl)-1-propyloxy]-4'-[2-(trans-4-propylcyclohexyl)ethyl]biphenyl:
4-[3-(trans-4-pentylcyclohexyl)-1-propyloxy]-4'-[2-(trans-4-pentylcyclohexyl)ethyl]biphenyl;

1-[3-(trans-4-methylcyclohexyl)-1-propyloxy]-4-[(trans-4-methylcyclohexyl)methoxy]benzene;
1-[3-(trans-4-ethylcyclohexyl)-1-propyloxy]-4-[(trans-4-methylcyclohexyl)methoxy]benzene;
1-[3-(trans-4-propylcyclohexyl)-1-propyloxy]-4-[(trans-4-methylcyclohexyl)methoxy]benzene;
1-[3-(trans-4-butylcyclohexyl)-1-propyloxy]-4-[(trans-4-methylcyclohexyl)methoxy]benzene
1-[3-(trans-4-pentylcyclohexyl)-1-propyloxy]-4-[(trans-4-methylcyclohexyl)methoxy]benzene;
1-[3-(trans-4-hexylcyclohexyl)-1-propyloxy]-4-[(trans-4-methylcyclohexyl)methoxy]benzene;
1-[3-(trans-4-heptylcyclohexyl)-1-propyloxy]-4-[(trans-4-methylcyclohexyl)methoxy]benzene;
1-[3-(trans-4-methylcyclohexyl)-1-propyloxy]-4-[(trans-4-ethylcyclohexyl)methoxy]benzene;
1-[3-(trans-4-ethylcyclohexyl)-1-propyloxy]-4-[(trans-4-ethylcyclohexyl)methoxy]benzene;
1-[3-(trans-4-propylcyclohexyl)-1-propyloxy]-4-[(trans-4-ethylcyclohexyl)methoxy]benzene;
1-[3-(trans-4-butylcyclohexyl)-1-propyloxy]-4-[(trans-4-ethylcyclohexyl)methoxy]benzene;
1-[3-(trans-4-methylcyclohexyl)-1-propyloxy].4-[(trans-4-propylcyclohexyl)methoxy]benzene;
1-[3-(trans-4-ethylcyclohexyl)-1-propyloxy]-4-[(trans-4-propylcyclohexyl)methoxy]benzene;
1-[3-(trans-4-propylcyclohexyl)-1-propyloxy]-4-[(trans-4-propylcyclohexyl)methoxy]benzene;
1-[3-(trans-4-butylcyclohexyl)-1-propyloxy]4-[(trans-4-propylcyclohexyl)methoxy]benzene;
1-[3-(trans-4-pentylcyclohexyl)-1-propyloxy]-4-[(trans-4-propylcyclohexyl)methoxy]benzene;
1-[3-(trans-4-hexylcyclohexyl)-1-propyloxy]-4-[(trans-4-propylcyclohexyl)methoxy]benzene;
1-[3-(trans-4-heptylcyclohexyl)-1-propyloxy]-4-[(trans-4-propylcyclohexyl)methoxy]benzene;
1-[3-(trans-4-methylcyclohexyl)-1-propyloxy]-4-[(trans-4-butylcyclohexyl)methoxy]benzene;
1-[3-(trans-4-ethylcyclohexyl)-1-propyloxy]-4-[(trans-4-butylcyclohexyl)methoxy]benzene;
1-[3-(trans-4-propylcyclohexyl)-1-propyloxy]-4-[(trans-4-butylcyclohexyl)methoxy]benzene;
1-[3-(trans-4-butylcyclohexyl)-1-propyloxy]-4-[(trans-4-butylcyclohexyl)methoxy]benzene;
1-[3-(trans-4-methylcyclohexyl)-1-propyloxy]-4-[(trans-4-pentylcyclohexyl)methoxy]benzene;
1-[3-(trans-4-ethylcyclohexyl)-1-propyloxy]-4-[(trans-4-pentylcyclohexyl)methoxy]benzene;
1-[3-(trans-4-propylcyclohexyl)-1-propyloxy]-4-[(trans-4-pentylcyclohexyl)methoxy]benzene;
1-[3-(trans-4-butylcyclohexyl)-1-propyloxy]-4-[(trans-4-pentylcyclohexyl)methoxy]benzene;
1-[3-(trans-4-pentylcyclohexyl)-1-propyloxy]-4-[(trans-4-pentylcyclohexyl)methoxy]benzene, m.p. (C-S$_A$) 104° C., transition S$_A$-N 116° C., cl.p. (N-I) 124° C.;
1-[3-(trans-4-hexylcyclohexyl)-1-propyloxy]-4-[(trans-4-pentylcyclohexyl)methoxy]benzene;
1-[3-(trans-4-heptylcyclohexyl)-1-propyloxy]-4-[(trans-4-pentylcyclohexyl)methoxy]benzene;
1-[3-(trans-4-methylcyclohexyl)-1-propyloxy]-4-[(trans-4-hexylcyclohexyl)methoxy]benzene;
1-[3-(trans-4-ethylcyclohexyl)-1-propyloxy]-4-[(trans-4-hexylcyclohexyl)methoxy]benzene;
1-[3-(trans-4-propylcyclohexyl)-1-propyloxy]-4-[(trans-4-hexylcyclohexyl)methoxy]benzene;
1-[3-(trans-4-butylcyclohexyl)-1-propyloxy]4-[(trans-4-hexylcyclohexyl)methoxy]benzene;

1-[3-(trans-4-pentylcyclohexyl)-1-propyloxy]-4-[(trans-4-hexylcyclohexyl)methoxy]benzene;
1-[3-(trans-4-hexylcyclohexyl)-1-propyloxy]-4-[(trans-4-hexylcyclohexyl)methoxy]benzene;
1-[3-(trans-4-heptylcyclohexyl)-1-propyloxy]-4-[(trans-4-hexylcyclohexyl)methoxy]benzene;
1-[3-(trans-4-methylcyclohexyl)-1-propyloxy]-4-[(trans-4-heptylcyclohexyl)methoxy]benzene;
1-[3-(trans-4-ethylcyclohexyl)-1-propyloxy]-4-[(trans-4-heptylcyclohexyl)methoxy]benzene;
1-[3-(trans-4-propylcyclohexyl)-1-propyloxy]-4-[(trans-4-heptylcyclohexyl)methoxy]benzene;
1-[3-(trans-4-butylcyclohexyl)-1-propyloxy]-4-[(trans-4-heptylcyclohexyl)methoxy]benzene;
1-[3-(trans-4-pentylcyclohexyl)-1-propyloxy]-4-[(trans-4-heptylcyclohexyl)methoxy]benzene;
1-[3-(trans-4-hexylcyclohexyl)-1-propyloxy]-4-[(trans-4-heptylcyclohexyl)methoxy]benzene;
1-[3-(trans-4-heptylcyclohexyl)-1-propyloxy]-4-[(trans-4-heptylcyclohexyl)methoxy]benzene;
1-[3-(trans-4-methylcyclohexyl)-1-propyloxy]-4-(trans-4-methylcyclohexyl)benzene;
1-[3-(trans-4-ethylcyclohexyl)-1-propyloxy]-4-(trans-4-methylcyclohexyl)benzene;
1-[3-(trans-4-propylcyclohexyl)-1-propyloxy]-4-(trans-4-methylcyclohexyl)benzene;
1-[3-(trans-4-butylcyclohexyl)-1-propyloxy]-4-(trans-4-methylcyclohexyl)benzene;
1-[3-(trans-4-pentylcyclohexyl)-1-propyloxy]-4-(trans-4-methylcyclohexyl)benzene;
1-[3-(trans-4-hexylcyclohexyl)-1-propyloxy]-4-(trans-4-methylcyclohexyl)benzene;
1-[3-(trans-4-heptylcyclohexyl)-1-propyloxy]-4-(trans-4-methylcyclohexyl)benzene;
1-[3-(trans-4-methylcyclohexyl)-1-propyloxy]-4-(trans-4-ethylcyclohexyl)benzene;
1-[3-(trans-4-ethylcyclohexyl)-1-propyloxy]-4-(trans-4-ethylcyclohexyl)benzene;
1-[3-(trans-4-propylcyclohexyl)-1-propyloxy]-4-(trans-4-ethylcyclohexyl)benzene;
1-[3-(trans-4-butylcyclohexyl)-1-propyloxy]-4-(trans-4-ethylcyclohexyl)benzene;
1-[3-(trans-4-pentylcyclohexyl)-1-propyloxy]-4-(trans-4-ethylcyclohexyl)benzene;
1-[3-(trans-4-hexylcyclohexyl)-1-propyloxy]-4-(trans-4-ethylcyclohexyl)benzene;
1-[3-(trans-4-heptylcyclohexyl)-1-propyloxy]-4-(trans-4-ethylcyclohexyl)benzene;
1-[3-(trans-4-methylcyclohexyl)-1-propyloxy]-4-(trans-4-propylcyclohexyl)benzene;
1-[3-(trans-4-ethylcyclohexyl)-1-propyloxy]-4-(trans-4-propylcyclohexyl)benzene;
1-[3-(trans-4-propylcyclohexyl)-1-propyloxy]-4-(trans-4-propylcyclohexyl)benzene;
1-[3-(trans-4-butylcyclohexyl)-1-propyloxy]-4-(trans-4-propylcyclohexyl)benzene;
1-[3-[3-(trans-4-pentylcyclohexyl)-1-propyloxy]-4-(trans-4-propylcyclohexyl)benzene;
1-[3-(trans-4-hexylcyclohexyl)-1-propyloxy]-4-(trans-4-propylcyclohexyl)benzene;
1-[3-(trans-4-heptylcyclohexyl)-1-propyloxy]-4-(trans-4-propylcyclohexyl)benzene;
1-[3-(trans-4-methylcyclohexyl)-1-propyloxy]-4-(trans-4-butylcyclohexyl)benzene;
1-[3-(trans-4-ethylcyclohexyl)-1-propyloxy]-4-(trans-4-butylcyclohexyl)benzene;
1-[3-(trans-4-propylcyclohexyl)-1-propyloxy]-4-(trans-4-butylcyclohexyl)benzene;
1-[3-(trans-4-butylcyclohexyl)-1-propyloxy]-4-(trans-4-butylcyclohexyl)benzene;
1-[3-(trans-4-pentylcyclohexyl)-1-propyloxy]-4-(trans-4-butylcyclohexyl)benzene;
1-[3-(trans-4-hexylcyclohexyl)-1-propyloxy]-4-(trans-4-butylcyclohexyl)benzene;
1-[3-(trans-4-heptylcyclohexyl)-1-propyloxy]-4-(trans-4-butylcyclohexyl)benzene;
1-[3-(trans-4-methylcyclohexyl)-1-propyloxy]-4-(trans-4-pentylcyclohexyl)benzene;
1-[3-(trans-4-ethylcyclohexyl)-1-propyloxy]-4-(trans-4-pentylcyclohexyl)benzene;
1-[3-(trans-4-propylcyclohexyl)-1-propyloxy]-4-(trans-4-pentylcyclohexyl)benzene;
1-[3-(trans-4-butylcyclohexyl)-1-propyloxy]-4-(trans-4-pentylcyclohexyl)benzene;
1-[3-(trans-4-pentylcyclohexyl)-1-propyloxy]-4-(trans-4-pentylcyclohexyl)benzene, m.p. (C-S$_B$) 67° C., transition S$_B$-N 113° C. cl.p. (N-I) 127° C.;
1-[3-(trans-4-methylcyclohexyl)-1-propyloxy]-4-(trans-4-hexylcyclohexyl)benzene;
1-[3-(trans-4-ethylcyclohexyl)-1-propyloxy]-4-(trans-4-hexylcyclohexyl)benzene;
1-[3-(trans-4-propylcyclohexyl)-1-propyloxy]-4-(trans-4-hexylcyclohexyl)benzene;
1-[3-(trans-4-butylcyclohexyl)-1-propyloxy]-4-(trans-4-hexylcyclohexyl)benzene;
1-[3-(trans-4-pentylcyclohexyl)-1-propyloxy]-4-(trans-4-hexylcyclohexyl)benzene;
1-[3-(trans-4-hexylcyclohexyl)-1-propyloxy]-4-(trans-4-hexylcyclohexyl)benzene;
1-[3-(trans-4-heptylcyclohexyl)-1-propyloxy]-4-(trans-4-hexylcyclohexyl)benzene;
1-[3-(trans-4-methylcyclohexyl)-1-propyloxy]-4-(trans-4-heptylcyclohexyl)benzene;
1-[3-(trans-4-ethylcyclohexyl)-1-propyloxy]-4-(trans-4-heptylcyclohexyl)benzene;
1-[3-(trans-4-propylcyclohexyl)-1-propyloxy]-4-(trans-4-heptylcyclohexyl)benzene;
1-[3-(trans-4 butylcyclohexyl)-1-propyloxy]-4-(trans-4-heptylcyclohexyl)benzene;
1-[3-(trans4-pentylcyclohexyl)-1-propyloxy]-4-(trans-4-heptylcyclohexyl)benzene;
1-[3-(trans-4-hexylcyclohexyl)-1-propyloxy]-4-(trans-4-heptylcyclohexyl)benzene;
1-[3-(trans-4-heptylcyclohexyl)-1-propyloxy]-4-(trans-4-heptylcyclohexyl)benzene;
4-[3-(trans-4-propylcyclohexyl)-1-propyloxy]-4'-(trans-4-propylcyclohexyl)biphenyl;
4-[3-(trans4-pentylcyclohexyl)-1-propyloxy]-4'-(trans-4-propylcyclohexyl)biphenyl;
4-[3-(trans-4-pentylcyclohexyl)-1-propyloxy]-4'-(trans-4-pentylcyclohexyl)biphenyl;
(4a$\alpha$H, 8a$\beta$H)-decahydro-2$\alpha$-(4-[3-(trans4-methylcyclohexyl)- 1-propyloxy]phenyl)-6$\beta$-pentylnaphthalene;
(4a$\alpha$H, 8a$\beta$H)-decahydro-2$\alpha$-(4-[3-(trans-4-ethylcyclohexyl)-1-propyloxy]phenyl)-6$\beta$-pentylnaphthalene;
(4a$\alpha$H, 8a$\beta$H) decahydro-2$\alpha$-(4-[3-(trans-4-propylcyclohexyl)-1-propyloxy]phenyl)-6$\beta$-pentylnaphthalene;
(4a$\alpha$H, 8a$\beta$H)-decahydro-2$\alpha$-(4-[3-(trans-4-butylcyclohexyl)-1-propyloxy]phenyl)-6$\beta$-pentylnaphthalene;
(4a$\alpha$H, 8a$\beta$H)-decahydro-2$\alpha$-(4-[3-(trans-4-pentylcyclohexyl)-1-propyloxy]phenyl)-6$\beta$-pentylnaphtalene, m.p. (C-S$_A$) 95° C., transition S$_A$-N 121° C., cl.p. (N-I) 159° C.;

(4aαH, 8aβH)-decahydro-2α-(4-[3-(trans-4-hexylcyclohexyl)-1-propyloxy]phenyl) 6β-pentylnaphthalene;

(4aαH, 8aβH)-decahydro-2α-(4-[3-(trans-4-heptylcyclohexyl)-1-propyloxy]phenyl)-6β-pentylnaphthalene;

(4aαH, 8aβH)-decahydro-2α-(4-[3-(trans-4-octylcyclohexyl)-1-propyloxy]phenyl)-6β-pentylnaphthalene;

1-methyl-4-(4-[3-(trans-4-pentylcyclohexyl)-1-propyloxy]phenyl)bicyclo[2,2,2]octane;

1-ethyl-4-(4-[3-(trans-4-pentylcyclohexyl)-1-propyloxy]phenyl)bicyclo[2,2,2]octane;

1-propyl-4-(4-[3-(trans-4-pentylcyclohexyl)-1-propyloxy]phenyl)bicyclo[2,2,2]octane;

1-butyl-4-(4-[3-(trans-4-pentylcyclohexyl)-1-propyloxy]phenyl)bicyclo[2,2,2]octane;

1-pentyl-4-(4-[3-(trans-4-pentylcyclohexyl)-1-propyloxy]phenyl)bicyclo[2,2,2]octane;

1-hexyl-4-(4-[3-(trans-4-pentylcyclohexyl)-1-propyloxy]phenyl)bicyclo[2,2,2]octane;

1-heptyl-4-(4-[3-(trans-4-pentylcyclohexyl)-1-propyloxy]phenyl)bicyclo[2,2,2]octane;

1-octyl-4-(4-[3-(trans-4-pentylcyclohexyl)-1-propyloxy]phenyl)bicyclo[2,2,2]octane;

1-nonyl-4-(4-[3-(trans-4-pentylcyclohexyl)-1-propyloxy]phenyl)bicyclo[2,2,2]octane;

1-decyl-4-(4-[3-(trans-4-pentylcyclohexyl)-1-propyloxy]phenyl)bicyclo[2,2,2]octane; 2-(4'-[3-(trans-4-pentylcyclohexyl)-1-propyloxy]-4-biphenylyl)-5-methylpyrimidine;

2-(4'-[3-(trans-4-pentylcyclohexyl)-1-propyloxy]-4-biphenylyl)-5-ethylpyrimidine;

2-(4'-[3-(trans-4-pentylcyclohexyl)-1-propyloxy]-4-biphenylyl)-5-propylpyrimidine;

2-(4'-[3-(trans-4-pentylcyclohexyl)-1-propyloxy]-4-biphenylyl)-5-butylpyrimidine;

2-(4'-[3-(trans-4-pentylcyclohexyl)-1-propyloxy]-4-biphenylyl)-5-pentylpyrimidine;

2-(4'-[3-(trans-4-pentylcyclohexyl)-1-propyloxy]-4-biphenylyl)-5-hexylpyrimidine;

2-(4'-[3-(trans-4-pentylcyclohexyl)-1-propyloxy]-4-biphenylyl)-5-heptylpyrimidine;

2-(4'-[3-(trans-4-pentylcyclohexyl)-1-propyloxy]-4-biphenylyl)-5-octylpyrimidine;

2-(4'-[3-(trans-4-pentylcyclohexyl)-1-propyloxy]-4-biphenylyl)-5-nonylpyrimidine;

2-(4'-[3-(trans-4-pentylcyclohexyl)-1-propyloxy]-4-biphenylyl)-5-decylpyrimidine, m.p. (C-S) 115° C., transition S-S$_C$ 142° C. transition S$_C$-N 205° C., cl.p. (N-I) 215° C.

EXAMPLE 2

1.9 g of 4-heptyloxybenzoic acid, 2.5 g of 4-[3-(trans-4-pentylcyclohexyl).1-propyloxy]phenol and 0.1 g of 4-(dimethylamino)pyridine were dissolved in 50 ml of dichloromethane and the solution was treated portionwise within 10 minutes while stirring with 2.0 g of N,N'-dicyclohexylcarbodiimide. The mixture was stirred at room temperature overnight and then filtered. The filtrate was diluted with dichloromethane, washed twice with 50 ml of saturated sodium carbonate solution each time and then with water, dried over magnesium sulfate, filtered and concentrated. The crude product obtained was purified by chromatography on silica gel with toluene. The 4-heptyloxybenzoic acid 4-[3-(trans-4-pentylcyclohexyl)-1-propyloxy]phenyl ester obtained was recrystallized from ethanol; m.p. (C-S$_C$) 74° C., transition S-S$_C$ 67° C. (monotropic), transition S$_C$-N 86° C. cl.p. (N-I) 148° C.;

The 4-[3-(trans-4-pentylcyclohexyl)-1-propyloxy]phenol used as the starting material was prepared as follows:

A mixture of 5.0 g of 3-(trans-4-pentylcyclohexyl)-1-propyl bromide, 10.0 g of hydroquinone, 10.0 g of anhydrous potassium carbonate and 250 ml of absolute butanone was heated under reflux overnight. Subsequently, the cooled reaction mixture was poured into water and extracted three times with 100 ml of dichloromethane each time. The combined organic phases were washed with 500 ml of water, dried over magnesium sulfate, filtered and concentrated. Chromatography of the residue on silica gel with toluene/ethyl acetate (vol. 4:1) gave 2.9 g of 4-[3-(trans-4-pentylcyclohexyl)-1-propyloxy]phenol; m.p. 100°–101° C.

The following compounds can be prepared in an analogous manner:

4-Methoxybenzoic acid 4-[3-(trans-4-propylcyclohexyl)-1-propyloxy]phenyl ester;

4-ethoxybenzoic acid 4-[3-(trans-4-propylcyclohexyl)-1-propyloxy]phenyl ester;

4-propyloxybenzoic acid 4-[3-(trans-4-propylcyclohexyl)-1-propyloxy]phenyl ester;

4-butyloxybenzoic acid 4-[3-(trans-4-propylcyclohexyl)-1-propyloxy]phenyl ester;

4-pentyloxybenzoic acid 4-[3-(trans-4-propylcyclohexyl)-1-propyloxy]phenyl ester;

4-hexyloxybenzoic acid 4-[3-(trans-4-propylcyclohexyl)-1-propyloxy]phenyl ester;

4-heptyloxybenzoic acid 4-[3-(trans-4-propylcyclohexyl)-1-propyloxy]phenyl ester;

4-octyloxybenzoic acid 4-[3-(trans-4-propylcyclohexyl)-1-propyloxy]phenyl ester;

4-nonyloxybenzoic acid 4-[3-(trans-4-propylcyclohexyl)-1-propyloxy]phenyl ester;

4-decyloxybenzoic acid 4-[3-(trans-4-propylcyclohexyl)-1-propyloxy]phenyl ester;

4-undecyloxybenzoic acid 4-[3-(trans-4-propylcyclohexyl)-1-propyloxy]phenyl ester;

4-dodecyloxybenzoic acid 4-[3-(trans-4-propylcyclohexyl)-1-propyloxy]phenyl ester;

4-methoxybenzoic acid 4-[3-(trans-4-pentylcyclohexyl)-1-propyloxy]phenyl ester;

4-ethoxybenzoic acid 4-[3-(trans-4-pentylcyclohexyl)-1-propyloxy]phenyl ester;

4-propyloxybenzoic acid 4-[3-(trans-4-pentylcyclohexyl)-1-propyloxy]phenyl ester;

4-butyloxybenzoic acid 4-[3-(trans-4-pentylcyclohexyl)-1-propyloxy]phenyl ester;

4-pentyloxybenzoic acid 4-[3-(trans-4-pentylcyclohexyl)-1-propyloxy]phenyl ester;

4-hexyloxybenzoic acid 4-[3-(trans-4-pentylcyclohexyl)-1-propyloxy]phenyl ester;

4-octyloxybenzoic acid 4-[3-(trans-4-pentylcyclohexyl)-1-propyloxy]phenyl ester, m.p. (C-S$_C$) 68° C. transition S-S$_C$ 67° C. (monotropic), transition S$_C$-N 99° C., cl.p. (N-I) 147° C.

4-nonyloxybenzoic acid 4-[3-(trans-4-pentylcyclohexyl-1-propyloxy]phenyl ester, m.p. (C-S$_C$) 77° C., transition S-S$_C$ 68° C. (monotropic), transition S$_C$-N 109° C., cl.p. (N-I) 144° C.;

4-decyloxybenzoic acid 4-[3-(trans-4-pentylcyclohexyl)-1-propyloxy]phenyl ester, m.p. (C-S) 64° C., transition S-S$_C$ 70° C. transition S$_C$-N 116° C., cl.p. (N-I) 143° C.;

4-undecyloxybenzoic acid 4-[3-(trans-4-pentylcyclohexyl)-1-propyloxy]phenyl ester, m.p. (C-S$_C$) 75° C., transition S-S$_C$ 71° C. (monotropic), transition S$_C$-N 121° C., cl.p. (N-I) 141° C.;

4-dodecyloxybenzoic acid 4-[3-(trans-4-pentylcyclohexyl)-1-propyloxy]phenyl ester, m.p. (C-S$_C$) 58° C., transition S-S$_C$ 75° C. (monotropic), transition S$_C$-N 125° C., cl.p. (N-I) 140° C.;

4-methoxybenzoic acid 4-[3-(trans-4-heptylcyclohexyl)-1-propyloxy]phenyl ester;

4-ethoxybenzoic acid 4-[3-(trans-4-heptylcyclohexyl)-1-propyloxy]phenyl ester;

4-propyloxybenzoic acid 4-[3-(trans-4-heptylcyclohexyl)-1-propyloxy]phenyl ester;

4-butyloxybenzoic acid 4-[3-(trans-4-heptylcyclohexyl)-1-propyloxy]phenyl ester;

4-pentyloxybenzoic acid 4-[3-(trans-4-heptylcyclohexyl)-1-propyloxy]phenyl ester;

4-hexyloxybenzoic acid 4-[3-(trans-4-heptylcyclohexyl)-1-propyloxy]phenyl ester;

4-heptyloxybenzoic acid 4-[3-(trans-4-heptylcyclohexyl)-1-propyloxy]phenyl ester;

4-octyloxybenzoic acid 4-[3-(trans-4-heptylcyclohexyl)-1-propyloxy]phenyl ester;

4-nonyloxybenzoic acid 4-[3-(trans-4-heptylcyclohexyl)-1-propyloxy]phenyl ester;

4-decyloxybenzoic acid 4-[3-(trans-4-heptylcyclohexyl)-1-propyloxy]phenyl ester;

4-undecyloxybenzoic acid 4-[3-(trans-4-heptylcyclohexyl)-1-propyloxy]phenyl ester;

4-dodecyloxybenzoic acid 4-[3-(trans-4-heptylcyclohexyl)-1-propyloxy]phenyl ester;

4-(allyloxy)benzoic acid 4-[3-(trans-4-propylcyclohexyl)-1-propyloxy]phenyl ester;

4-(3-butenyl)oxybenzoic acid 4-[3-(trans-4-propylcyclohexyl)-1-propyloxy]phenyl ester;

4-(4-pentenyl)oxybenzoic acid 4-[3-(trans-4-propylcyclohexyl)-1-propyloxy]phenyl ester;

4-(5-hexenyl)oxybenzoic acid 4-[3-(trans-4-propylcyclohexyl)-1-propyloxy]phenyl ester;

4-(6-heptenyl)oxybenzoic acid 4-[3-(trans-4-propylcyclohexyl)-1-propyloxy]phenyl ester;

4-(7-octenyl)oxybenzoic acid 4-[3-(trans-4-propylcyclohexyl)-1-propyloxy]phenyl ester;

4-(8-nonenyl)oxybenzoic acid 4-[3-(trans-4-propylcyclohexyl)-1-propyloxy]phenyl ester;

4-(9-decenyl)oxybenzoic acid 4-[3-(trans-4-propylcyclohexyl)-1-propyloxy]phenyl ester;

4-(10-undecyl)oxybenzoic acid 4-[3-(trans-4-propylcyclohexyl)-1-propyloxy]phenyl ester;

4-(11-dodecyl)oxybenzoic acid 4-[3-(trans-4-propylcyclohexyl)-1-propyloxy]phenyl ester;

4-alloxybenzoic acid 4-[3-(trans-4-pentylcyclohexyl)-1-propyloxy]phenyl ester;

4-(3-butenyl)oxybenzoic acid 4-[3-(trans-4-pentylcyclohexyl)-1-propyloxy]phenyl ester;

4-(4-pentenyl)oxybenzoic acid 4-[3-(trans-4-pentylcyclohexyl)-1-propyloxy]phenyl ester;

4-(5-hexenyl)oxybenzoic acid 4-[3-(trans-4-pentylcyclohexyl)-1-propyloxy]phenyl ester;

4-(6-heptenyl)oxybenzoic acid 4-[3-(trans-4-pentylcyclohexyl) 1-propyloxy]phenyl ester. m.p. (C-S$_C$) 64° C. transition S-S$_C$ 52° C. (monotropic). transition S$_C$-N 73° C., cl.p. (N-I) 147° C.;

4-(7-octenyl)oxybenzoic acid 4-[3-(trans-4-pentylcyclohexyl)-1-propyloxy]phenyl ester, m.p. (C-S$_C$) 75° C. transition S-S$_C$ 57° C. (monotropic), transition S$_C$-N 86° C., cl.p. (N-I) 142° C.;

4-(8-nonenyl)oxybenzoic acid 4-[3-(trans-4-pentyl cyclohexyl)-1-propyloxy]phenyl ester, m.p. (C-S$_C$) 61° C., transition S-S$_C$ 56° C. (monotropic), transition S$_C$-N 99° C., cl.p. (N-I) 144° C.;

4-(9-decenyl)oxybenzoic acid 4-[3-(trans-4-pentylcyclohexyl)-1-propyloxy]phenyl ester, m.p. (C-S$_C$) 64° C. transition S-S$_C$ 58° C. (monotropic), transition S$_C$-N 105° C., cl.p. (N-I) 138° C.;

4-(10-undecenyl)oxybenzoic acid 4-[3-(trans-4-pentylcyclohexyl)- 1-propyloxy]phenyl ester, m.p. (C-S$_C$) 71° C., transition S-S$_C$ 61° C. (monotropic), transition S$_C$-N 114° C., cl.p. (N-I) 139° C.;

4-(11-dodecenyl)oxybenzoic acid 4-[3-(trans-4-pentylcyclohexyl)-1-propyloxy]phenyl ester, m.p. (C-S) 55° C., transition S-S$_C$ 65° C., transition S$_C$-N 117° C., cl.p (N-I) 136° C.;

4-allyloxybenzoic acid 4-[3-(trans-4-heptylcyclohexyl)-1-propyloxy]phenyl ester;

4-(3-butenyl)oxybenzoic acid 4-[3-(trans-4-heptylcyclohexyl)-1-propyloxy]phenyl ester;

4-(4-pentenyl)oxybenzoic acid 4-[3-(trans-4-heptylcyclohexyl)-1-propyloxy]phenyl ester;

4-(5-hexenyl)oxybenzoic acid 4-[3-(trans-4-heptylcyclohexyl)-1-propyloxy]phenyl ester;

4-(6-heptenyl)oxybenzoic acid 4-[3-(trans-4-heptylcyclohexyl)-1-propyloxy]phenyl ester;

4-(7-octenyl)oxybenzoic acid 4-[3-(trans-4-heptylcyclohexyl)-1-propyloxy]phenyl ester;

4-(8-nonenyl)oxybenzoic acid 4-[3-(trans-4-heptylcyclohexyl)-1-propyloxy]phenyl ester;

4-(9-decenyl)oxybenzoic acid 4-[3-(trans-4-heptylcyclohexyl)-1-propyloxy]phenyl ester;

4-methoxy-3-fluorobenzoic acid 4-[3-(trans-4-propylcyclohexyl)-1-propyloxy]phenyl ester;

4-ethoxy-3-fluorobenzoic acid 4-[3-(trans-4-propylcyclohexyl)-1-propyloxy]phenyl ester;

4-propyloxy-3-fluorobenzoic acid 4-[3-(trans-4-propylcyclohexyl)-1-propyloxy]phenyl ester;

4-butyloxy-3-fluorobenzoic acid 4-[3-(trans-4-propylcyclohexyl)-1-propyloxy]phenyl ester;

4-pentyloxy-3 fluorobenzoic acid 4-[3-(trans-4-propylcyclohexyl)-1-propyloxy]phenyl ester;

4-hexyloxy-3-fluorobenzoic acid 4-[3-(trans-4-propylcyclohexyl)-1-propyloxy]phenyl ester;

4-heptyloxy-3-fluorobenzoic acid 4-[3-(trans-4-propylcyclohexyl)-1-propyloxy]phenyl ester;

4-octyloxy-3-fluorobenzoic acid 4-[3-(trans-4-propylcyclohexyl)-1-propyloxy]phenyl ester;

4-nonyloxy-3-fluorobenzoic acid 4-[3-(trans-4-propylcyclohexyl)-1-propyloxy]phenyl ester;

4-decyloxy-3-fluorobenzoic acid 4-[3-(trans-4-propylcyclohexyl)-1-propyloxy]phenyl ester;

4-undecyloxy-3-fluorobenzoic acid 4-[3-(trans-4-propylcyclohexyl)-1-propyloxy]phenyl ester;

4-dodecyloxy-3-fluorobenzoic acid 4-[3-(trans-4-propylcyclohexyl)-1-propyloxy]phenyl ester;

4-methoxy-3-fluorobenzoic acid 4-[3-(trans-4-pentylcyclohexyl)-1-propyloxy]phenyl ester;

4-ethoxy-3-fluorobenzoic acid 4-[3-(trans-4-pentylcyclohexyl)-1-propyloxy]phenyl ester;

4-propyloxy-3-fluorobenzoic acid 4-[3-(trans-4-pentylcyclohexyl)-1-propyloxy]phenyl ester;

4-butyloxy-3-fluorobenzoic acid 4-[3-(trans-4-pentylcyclohexyl)-1-propyloxy]phenyl ester;

4-pentyloxy-3-fluorobenzoic acid 4-[3-(trans-4-pentylcyclohexyl)-1-propyloxy]phenyl ester; 4-hexyloxy-3- fluorobenzoic acid 4-[3-(trans-4-pentylcyclohexyl)-1-propyloxy]phenyl ester; 4-octyloxy-3-fluorobenzoic acid 4-[3-(trans-4-pentylcyclohexyl)-1-propyloxy]phenyl ester;

4-nonyloxy.3-fluorobenzoic acid 4-[3-(trans-4-pentylcyclohexyl)-1-propyloxy]phenyl ester; 4-decyloxy-3-fluorobenzoic acid 4-[3-(trans-4-pentylcyclohexyl)-1-propyloxy]phenyl ester; 4-undecyloxy-3-fluorobenzoic acid 4-[3-(trans-4-pentylcyclohexyl)-1-propyloxy]phenyl ester;

4-dodecyloxy-3-fluorobenzoic acid 4-[3-(trans-4-pentylcyclohexyl)-1-propyloxy]phenyl ester, m.p. (C-S$_C$) 69° C., transition S-S$_C$ <40° C., transition S$_C$-N 120° C., cl.p. (N-I) 129° C.;

4-methoxy-3-fluorobenzoic acid 4-[3-(trans-4-heptylcyclohexyl)-1-propyloxy]phenyl ester;

4-ethoxy-3-fluorobenzoic acid 4-[3-(trans-4-heptylcyclohexyl)- 1-propyloxy]phenyl ester;

4-propyloxy-3-fluorobenzoic acid 4-[3-(trans-4-heptylcyclohexyl)-1-propyloxy]phenyl ester;

4-butyloxy-3-fluorobenzoic acid 4-[3-(trans-4-heptylcyclohexyl)-1-propyloxy]phenyl ester;

4-pentyloxy-3-fluorobenzoic acid 4-[3-(trans-4-heptylcyclohexyl)-1-propyloxy]phenyl ester;

4-hexyloxy-3-fluorobenzoic acid 4-[3-(trans-4-heptylcyclohexyl)-1-propyloxy]phenyl ester;

4-heptyloxy-3-fluorobenzoic acid 4-[3-(trans-4-heptylcyclohexyl)-1-propyloxy]phenyl ester;

4-octyloxy-3-fluorobenzoic acid 4-[3-(trans-4-heptylcyclohexyl)-1-propyloxy]phenyl ester;

4-nonyloxy-3-fluorobenzoic acid 4-[3-(trans-4-heptylcyclohexyl)-1-propyloxy]phenyl ester;

4-decyloxy 3-fluorobenzoic acid 4-[3-(trans-4-heptylcyclohexyl)-1-propyloxy]phenyl ester;

4-undecyloxy-3 fluorobenzoic acid 4-[3-(trans-4-heptylcyclohexyl)-1 propyloxy]phenyl ester;

4-dodecyloxy-3-fluorobenzoic acid 4-[3-(trans-4-heptylcyclohexyl)-1-propyloxy]phenyl ester;

4-(11-dodecenyl)oxy-3-fluorobenzoic acid 4-[3-(trans-4-pentylcyclohexyl)-1-propyloxy]phenyl ester;

4-heptyloxy-2,3-difluorobenzoic acid 4-[3-(trans-4-pentylcyclohexyl)-1-propyloxy]phenyl ester, m.p. (C-S$_C$) 79° C., transition S$_C$-N 94° C., cl.p. (N-I) 139° C.;

4-octyloxy-2,3-difluorobenzoic acid 4-[3-(trans-4-pentylcyclohexyl) 1-propyloxy]phenyl ester, m.p. (C-S$_C$) 70° C., transition S$_C$-N 103° C., cl.p. (N-I) 138° C.;

4-nonyloxy-2,3-difluorobenzoic acid 4-[3-(trans-4-pentylcyclohexyl)-1-propyloxy]phenyl ester, m.p. (C-S$_C$) 73° C., transition S$_C$-N 110° C., cl.p. (N-I) 136° C.;

4-decyloxy-2,3-difluorobenzoic acid 4-[3-(trans-4-pentylcyclohexyl)-1-propyloxy]phenyl ester, m.p. (C-S$_C$) 68° C., transition S$_C$-N 115° C., cl.p. (N-I) 135° C.;

4-undecyloxy-2,3-difluorobenzoic acid 4-[3-(trans-4-pentylcyclohexyl)-1-propyloxy]phenyl ester, m.p. (C-S$_C$) 68° C., transition S$_C$-N 118° C., cl.p. (N-I) 133° C.;

4-dodecyloxy-2,3-difluorobenzoic acid 4-[3-(trans-4-pentylcyclohexyl)-1-propyloxy]phenyl ester, m.p. (C-S$_C$) 66° C., transition S$_C$-N 121° C., cl.p. (N-I) 133° C.;

4-dodecyloxy-2-chlorobenzoic acid 4-[3-(trans-4-pentylcyclohexyl)-1-propyloxy]phenyl ester;

4-dodecyloxy-2-bromobenzoic acid 4-[3-(trans-4-pentylcyclohexyl)-1-propyloxy]phenyl ester;

4-dodecyloxy-2-cyanobenzoic acid 4-[3-(trans-4-pentylcyclohexyl)-1-propyloxy]phenyl ester;

4-dodecyloxy-3-chlorobenzoic acid 4-[3-(trans-4-pentylcyclohexyl)-1-propyloxy]phenyl ester, m.p. (C-S$_C$) 60° C., transition S$_C$-N 105° C., cl.p. (N-I) 122° C.;

4-dodecyloxy-3-bromobenzoic acid 4-[3-(trans-4-pentylcyclohexyl)-1-propyloxy]phenyl ester, m.p. (C-S$_C$) 70° C., transition S$_C$-N 92° C., cl.p. (N-I) 112° C.;

4-dodecyloxy-3-cyanobenzoic acid 4-[3-(trans-4-pentylcyclohexyl)-1-propyloxy]phenyl ester, m.p. (C-I) 103° C., transition S$_C$-N 97° C., cl.p. (N-I) 100° C.;

(S)-4-(1-methylheptyl)oxybenzoic acid 4-[3-(trans-4-pentylcyclohexyl)-1-propyloxy]phenyl ester;

(S)-4-(1-methylheptyl)oxy-3-flurobenzoic acid 4-[3-(trans-4-pentylcyclohexyl)-1-propyloxy]phenyl ester;

(S)-4-(1-methylheptyl)oxy-3-chlorobenzoic acid 4-[3-(trans-4-pentylcyclohexyl)-1-propyloxy]phenyl ester;

(S)-4-(1-methylheptyl)oxy-3-bromobenzoic acid 4-[3-(trans-4-pentylcyclohexyl)-1-propyloxy]phenyl ester;

(S)-4-(1-methylheptyl)oxy-3-cyanobenzoic acid 4-[3-(trans-4-pentylcyclohexyl)-1-propyloxy]phenyl ester;

trans-4-methylcyclohexanecarboxylic acid 4-[3-(trans-4-propylcyclohexyl)-1-propyloxy]phenyl ester;

trans-4-ethylcyclohexanecarboxylic acid 4-[3-(trans-4-propylcyclohexyl)-1-propyloxy]phenyl ester;

trans-4-propylcyclohexanecarboxylic acid 4-[3-(trans-4-propylcyclohexyl)-1-propyloxy]phenyl ester;

trans-4-butylcyclohexanecarboxylic acid 4-[3-(trans-4-propylcyclohexyl)-1-propyloxy]phenyl ester;

trans-4-pentylcyclohexanecarboxylic acid 4-[3-(trans-4-propylcyclohexyl)-1-propyloxy]phenyl ester;

trans-4-hexylcyclohexanecarboxylic acid 4-[3-(trans-4-propylcyclohexyl)-1-propyloxy]phenyl ester;

trans-4-heptylcyclohexanecarboxylic acid 4-[3-(trans-4-propylcyclohexyl)-1-propyloxy]phenyl ester;

trans-4-methylcyclohexanecarboxylic acid 4-[3-(trans-4-pentylcyclohexyl)-1-propyloxy]phenyl ester;

trans-4-ethylcyclohexanecarboxylic acid 4-[3-(trans-4-pentylcyclohexyl)-1-propyloxy]phenyl ester;

trans-4-propylcyclohexanecarboxylic acid 4-[3-(trans-4-pentylcyclohexyl)-1-propyloxy]phenyl ester;

trans-4-butylcyclohexanecarboxylic acid 4-[3-(trans-4-pentylcyclohexyl)-1-propyloxy]phenyl ester;

trans-4-pentylcyclohexanecarboxylic acid 4-[3-(trans-4-pentylcyclohexyl)-1-propyloxy]phenyl ester, m.p. (C-S) 88° C., transition S-S$_B$ 102° C. transition S$_B$-S$_A$ 114° C. transition S$_A$-N 127° C., cl.p. (N-I) 150° C.;

trans-4-hexylcyclohexanecarboxylic acid 4-[3-(trans-4-pentylcyclohexyl)-1-propyloxy]phenyl ester;

trans-4-heptylcyclohexanecarboxylic acid 4-[3-(trans-4-pentylcyclohexyl)-1-propyloxy]phenyl ester;

trans-4-methylcyclohexanecarboxylic acid 4-[3-(trans-4-heptylcyclohexyl)-1-propyloxy]phenyl ester;

trans-4-ethylcyclohexanecarboxylic acid 4-[3-(trans-4-heptylcyclohexyl)-1-propyloxy]phenyl ester;

trans-4-propylcyclohexanecarboxylic acid 4-[3-(trans-4-heptylcyclohexyl)-1-propyloxy]phenyl ester;

trans-4-butylcyclohexanecarboxylic acid 4-[3-(trans-4-heptylcyclohexyl)-1-propyloxy]phenyl ester;

trans-4-pentylcyclohexanecarboxylic acid 4-[3-(trans-4-heptylcyclohexyl)-1-propyloxy]phenyl ester;

trans-4-hexylcyclohexanecarboxylic acid 4-[3-(trans-4-heptylcyclohexyl)-1-propyloxy]phenyl ester;

trans-4-heptylcyclohexanecarboxylic acid 4-[3-(trans-4-heptylcyclohexyl)-1-propyloxy]phenyl ester;

trans-4-vinylcyclohexanecarboxylic acid 4-[3-(trans-4-pentylcyclohexyl)-1-propyloxy]phenyl ester;

trans-4 (2-propenyl)cyclohexanecarboxylic acid 4-[3-(trans-4-pentylcyclohexyl)-1-propyloxy]phenyl ester;

trans-4-(3-butenyl)cyclohexanecarboxylic acid 4-[3-(trans-4-pentylcyclohexyl)-1-propyloxy]phenyl ester;

trans-4-(4-pentenyl)cyclohexanecarboxylic acid 4-[3-(trans-4-pentylcyclohexyl)-1-propyloxy]phenyl ester;

4-(trans-4-pentylcyclohexyl)benzoic acid 4-[3-(trans-4-pentylcyclohexyl)-1-propyloxy]phenyl ester, m.p. (C-$S_C$) 132° C. transition $S_C$-$S_A$ 142° C., transition $S_A$-N 161° C., cl.p. (N-I) 232° C.

4-(4-pentylbicyclo[2,2,2]oct-1-yl)benzoic acid 4-[3-(trans-4-pentylcyclohexyl)-1-propyloxy]phenyl ester, m.p. (C-$S_A$) 171° C. transition $S_A$-N 194° C., cl.p. (N-I) 260° C.;

4-(5-pentyl-2-pyrimidinyl)benzoic acid 4-[3-(trans-4-pentylcyclonexyl)-1-propyloxy]phenyl ester, m.p. (C-$S_C$) 97° C., transition $S_C$-N 80° C., cl.p. (N-I) 229° C.;

4-(5-hexyl 2-pyrimidinyl)benzoic acid 4-[3-(trans-4-pentylcyclonexyl)-1-propyloxy]phenyl ester;

4-(5-hepryl-2-pyrimidinyl)benzoic acid 4-[3-(trans-4-pentylcyclonexyl) 1-propyloxy]phenyl ester, m.p. (C-N) 118° C., cl.p. (N-I) 219° C.;

4-(5-octyl-2-pyrimidinyl)benzoic acid 4-[3-(trans-4-pentylcyclonexyl)-1-propyloxy]phenyl ester;

4-(5-nonyl-2-pyrimidinyl)benzoic acid 4-[3-(trans-4-pentylcyclonexyl)-1-propyloxy]phenyl ester;

4-(5-decyl-2-pyrimidinyl)benzoic acid 4-[3-(trans-4-pentylcyclohexyl),1-propyloxy]phenyl ester, m.p.(C-$S_C$) 108° C., transition $S_C$-N 126° C., cl.p. (N-I) 205° C.;

trans-4-(trans-4-pentylcyclohexyl)cyclohexanecarboxylic acid 4-[3-(trans-4-pentylcyclohexyl)-1-propyloxy]phenyl ester, m.p. (C-$S_C$) 77° C., transition $S_B$-$S_A$ 189° C., transition $S_A$-N 220° C., cl.p. (N-I) 239° C.;

4-[2-(trans-4-pentylcyclohexyl)ethyl]benzoic acid 4-[3-(trans-4-pentylcyclohexyl)-1-propyloxy]phenyl ester, m.p. (C-$S_B$) 85° C., transition $S_B$-$S_C$ 117° C., transition $S_C$-$S_A$ 134° C., transition $S_A$-N 182° C., cl.p. (N-I) 206° C.;

4-[(trans-4-pentylcyclohexyl)methoxy]benzoic acid 4-[3-(trans-4-pentylcyclohexyl)-1-propyloxy]phenyl ester, m.p. (C-$S_B$) 95° C., transition $S_B$-$S_C$ 103° C., transition $S_C$-$S_A$ 154° C. transition $S_A$-N 178° C., cl.p. (N-I) 212° C.;

4-[trans-4-pentylcyclohexylcarbonyloxy]benzoic acid 4-[3-(trans 4-pentylcyclohexyl)-1-propyloxy]phenyl ester, m.p. (C-S) 95° C., transition S-$S_C$ 98° C., transition $S_C$-N 113° C., cl.p (N-I) 228° C.;

4-[3-(trans-4-pentylcyclohexyl)-1-propyloxy]benzoic acid 4-[3-(trans-4-pentylcyclohexyl)-1-propyloxy]phenyl ester, m.p. (C-S) 88° C., transition S-$S_C$ 112° C. transition $S_C$-$S_A$ 157° C., transition $S_A$-N 183° C., cl.p. (N-I) 196° C.;

4-[3-(trans-4-pentylcyclohexyl)-1-propyloxy]benzoic acid 4-[2-(trans-4-pentylcyclohexyl)ethyl]phenyl ester, m.p. (C-S) 77° C., transition S-$S_C$ 116° C., transition $S_C$-$S_A$ 132° C., transition $S_A$-N 190° C., cl.p. (N-I) 210° C.;

4-[3-(trans-4-pentylcyclohexyl)-1-propyloxy]benzoic acid 4-[(trans-4-pentylcyclohexyl)methoxy]phenyl ester;

4-[3-(trans-4-pentylcyclohexyl)-1-propyloxy]benzoic acid 4-(trans-4-pentylcyclohexyl)phenyl ester;

4-[3-(trans-4-pentylcyclohexyl)-1-propyloxy]benzoic acid 4-(trans-4 pentylcyclohexylcarbonyloxy)phenyl ester.

EXAMPLE 3

A solution of 2.1 g of 4-[3-(trans-4-pentylcyclohexyl)-1-propyloxy]benzaldehyde and 1.2 g of 2-pentyl-1,3-propanediol in 50 ml of toluene was treated with 2 drops of 10% (vol., sulfuric acid. The mixture was heated to boiling for 2.5 hours, with the resulting water being distilled off simultaneously. Then, 4 drops of triethylamine were added to the reaction mixture. After cooling the mixture was washed with 20 ml of 1N sodium hydrogen carbonate solution and twice with 20 ml of water each time, dried over sodium sulfate, filtered and concentrated. Chromatography of the residue on silica gel with toluene gave 0.6 g of trans-5-pentyl-2-(4-[3-(trans-4-pentylcyciohexyl)-1-propyloxy]phenyl)-1,3-dioxane. M.p. (C-$S_B$) 65° C. transition $S_B$-N 73° C., cl.p (N-I) 128° C.

The 4-[3-(trans-4-pentylcyclohexyl)-1-propyloxy]-benzaldehyde used as the starting material was prepared as follows:

1.9 g of 4-hydroxybenzaldehyde, 5.0 g of 3-(trans-4-pentylcyclohexyl)-1-propyl bromide 8.3 g of potassium carbonate and 50 ml of butanone were reacted in an analogous manner to Example 1 to give 6.0 g of 4-[3-(trans-4-pentylcyclohexyl)-1-propyloxy]benzaldehyde.

The following compounds can be prepared in an analogous manner:

trans-5-Methyl-2-(4-[3-(trans-4-propylcyclohexyl)-1-propyloxy]phenyl]-1,3-dioxane;
trans-5-ethyl-2-(4-[3-(trans-4-propylcyclohexyl)-1-propyloxy]phenyl]-1,3-dioxane;
trans-5-propyl-2-(4-[3-(trans-4-propylcyclohexyl)-1-propyloxy]phenyl]-1,3-dioxane;
trans-5-butyl-2-(4-[3-(trans-4-propylcyclohexyl)-1-propyloxy]phenyl]-1,3-dioxane;
trans-5-pentyl-2-(4-[3-(trans-4-propylcyclohexyl)-1-propyloxy]phenyl]-1,3-dioxane;
trans-5-hexyl-2-(4-[3-(trans-4-propylcyclohexyl)-1-propyloxy]phenyl]-1,3-dioxane;
trans-5-heptyl-2-(4-[3-(trans-4-propylcyclohexyl)-1-propyloxy]phenyl]-1,3-dioxane;
trans-5-methyl-2-(4-[3-(trans-4-ethylcyclohexyl)-1-propyloxy)phenyl]-1,3-dioxane;
trans-5-ethyl-2-(4-[3-(trans-4-pentylcyclohexyl)-1-propyloxy)phenyl]-1,3-dioxane;
trans-5 propyl-2-(4-[3-(trans-4-pentylcyclohexyl)--1-propyloxy)phenyl]-1,3-dioxane;
trans-5-butyl-2-(4-[3-(trans-4-pentylcyclohexyl)-1-propyloxy)phenyl]-1,3-dioxane;
trans-5-hexyl-2-(4-[3-(trans-4-pentylcyclohexyl)-1-propyloxy)phenyl]-1,3-dioxane;
trans-5-heptyl-2-(4-[3-(trans-4-pentylcyclohexyl)-1-propyloxy)phenyl]-1.3-dioxane;
trans-5-methyl-2-(4-[3-(trans-4-heptylcyclohexyl)-1-propyloxy]phenyl)-1,3-dioxane;
trans-5-ethyl-2-(4-[3-(trans-4-heptylcyclohexyl)-1-propyloxy]phenyl]-1,3-dioxane;
trans-5-propyl-2-(4-[3-(trans-4heptylcyclohexyl)-1propyloxy]phenyl)-1,3-dioxane;
trans-5-butyl-2-(4-[3-(trans-4-heptylcyclohexyl)-1-propyloxy]phenyl)-1,3-dioxane;
trans-5-pentyl 2-(4-[3-(trans-4-heptylcyclohexyl)-1-propyloxy]phenyl)-1 3-dioxane;
trans-5-hexyl-2-(4-[3-(trans 4-heptylcyclohexyl)-1propyloxy]phenyl)-1,3-dioxane;
trans-5-heptyl 2-(4-[3-(trans-4-heptylcyclohexyl)-1propyloxy]phenyl)-1.3-dioxane.

EXAMPLE 4

0.14 g to 4-hydroxy-2-fluorobenzonitrile, 0.35 g of 4-[3-(trans-4-pentylcyclohexyl)-1-propyloxy]benzoic acid, 0.24 g of N,N'-dicyclohexylcarbodiimide, 0.04 g of 4-(dimethylamino)pyridine and 25 ml of dichloromethane were reacted in an analogous manner to Example 2. This gave 0.32 g of 4-[3-(trans-4-pentylcyclohexyl)-1-propyloxy]benzoic acid 4-cyano.3-fluorophenyl ester with m.p. (C-N) 75° C., cl.p. (N-I) 146° C.

The 4-[3-trans-4-pentylcyclohexyl)-1-propyloxy]benzoic acid used as the starting material was prepared as follows:

A solution of 5 g of 4-[3-(trans-4-pentylcyclohexyl)-1-propyloxy]benzaldehyde in 100 ml of acetone was treated dropwise with 10 ml of Jones' reagent. The mixture was stirred at room temperature for 1 hour and then poured into 100 ml of water. The precipitate which thereby resulted was filtered off, washed portionwise with water and dried in a vacuum. The crude product was recrystallized from ethanol and gave 2.2 g of pure 4-[3-(trans-4-pentylcyclohexyl)-1-propyloxy]benzoic acid with m.p. (C-N) 204° C., cl.p. (N-I) 215° C.

The following compounds can be prepared in an analogous manner:

4-[3-(trans-4-Methylcyclohexyl)-1-propyloxy]benzoic acid 4-cyano-3-fluorophenyl ester;
4-[3-(trans-4-ethylcyclohexyl)-1-propyloxy]benzoic acid 4-cyano-3-fluorophenyl ester;
4-[3-(trans-4-propylcyclohexyl)-1-propyloxy]benzoic acid 4-cyano-3-fluorophenyl ester;
4-[3-(trans 4.butylcyclohexyl) 1° propyloxy]benzoic acid 4-cyano-3-fluorophenyl ester;
4-[3-(trans-4-hexylcyclohexyl)-1-propyloxy]benzoic acid 4-cyano-3-fluorophenyl ester;
4-[3-(trans-4-heptylcyclohexyl)-1-propyloxy]benzoic acid 4-cyano-3-fluorophenyl ester;
4-[3-(trans-4-octylcyclohexyl)-1 propyloxy]benzoic acid 4-cyano-3-fluorophenyl ester;
4-[3-(trans-4-nonylcyclohexyl)-1-propyloxy]benzoic acid 4-cyano-3-fluorophenyl ester;
4-[3-(trans-4-decylcyclohexyl)-1-propyloxy]benzoic acid 4-cyano-3-fluorophenyl ester;
4-[3-(trans-4-methylcyclohexyl)-1-propyloxy]benzoic acid 4-cyano-2-fluorophenyl ester;
4-[3-(trans-4-ethylcyclohexyl)1-propyloxy]benzoic acid 4-cyano-2-fluorophenyl ester;
4-[3-(trans-4-propylcyclohexyl)-1-propyloxy]benzoic acid 4-cyano-2-fluorophenyl ester;
4-[3-(trans-4-butylcyclohexyl)-1-propyloxy]benzoic acid 4-cyano-2-fluorophenyl ester;
4-[3-(trans-4-pentylcyclohexyl)-1-propyloxy]benzoic acid 4-cyano-2-fluorophenyl ester;
4-[3-(trans-4-hexylcyclohexyl). propyloxy]benzoic acid 4-cyano-2-fluorophenyl ester;
4-[3-(trans-4-heptylcyclohexyl)-1-propyloxy]benzoic acid 4-cyano-2-fluorophenyl ester;
4-[3-(trans-4-octylcyclohexyl)-1-propyloxy]benzoic acid 4-cyano-2-fluorophenyl ester;
4-[3-(trans-4-nonylcyclohexyl)-1-propyloxy]benzoic acid 4-cyano-2-fluorophenyl ester;
4-[3-(trans-4-decylcyclohexyl)-1-propyloxy]benzoic acid 4-cyano-2-fluorophenyl ester;
4-[3-(trans-4-methylcyclohexyl)-1-propyloxy]benzoic acid 4-cyanophenyl ester;
4-[3-(trans-4 ethylcyclohexyl)-1-propyloxy]benzoic acid 4-cyanophenyl ester;
4-[3-(trans-4-propylcyclohexyl) 1-propyloxy]benzoic acid 4-cyanophenyl ester;
4-[3-(trans-4-butylcyclohexyl)-1-propyloxy]benzoic acid 4-cyanophenyl ester;
4-[3-(trans-4-pentylcyclohexyl)-1-propyloxy]benzoic acid 4-cyanophenyl ester, m.p. (C-S$_A$) 82° C., transition S$_A$-N 117° C., cl.p. (N-I) 168° C.;
4-[3-(trans-4-pentylcyclohexyl)-1-propyloxy]benzoic acid 3,4-difluorophenyl ester, m.p.(C-N) 75° C., transition S$_A$-N 65° C. cl.p. (N-I) 110° C.;
4-[3-(trans-4-pentylcyclohexyl)-1-propyloxy]benzoic acid 4-fluorophenyl ester, m.p. (C-N; 90° C. transition S$_A$-N 73° C., cl.p. (N-I) 127° C.;
4-[3-(trans-4-pentylcyclohexyl)-1-propyloxy]benzoic acid 4-chlorophenyl ester, m p. (C-S$_A$) 96° C., transition S$_A$-N 123° C., cl.p. (N-I) 150° C.;
4-[3-(trans-4-pentylcyclohexyl)-1-propyloxy]benzoic acid 4-bromophenyl ester, m.p. (C-S$_A$) 108° C., transition S$_A$-N 131° C., cl.p. (N-I) 152° C.;
4-[3-(trans-4-pentylcyclohexyl)-1-propyloxy]benzoic acid 4-iodophenyl ester, m.p. (C-S$_A$) 114° C., transition S$_A$-N 133° C., cl.p. (N-I) 149° C.;
4-[3-(trans-4-propylcyclohexyl)-1-propyloxy]benzoic acid 4-methylphenyl ester;
4-[3-(trans-4-propylcyclohexyl)-1-propyloxy]benzoic acid 4-ethylphenyl ester;
4-[3-(trans-4-propylcyclohexyl)-1-propyloxy]benzoic acid 4-propylphenyl ester;
4-[3-(trans-4-propylcyclohexyl)-1-propyloxy]benzoic acid 4-butylphenyl ester; 4-[3-(trans-4-propylcyclohexyl)-1-propyloxy]benzoic acid 4-pentylphenyl ester;
4-[3-(trans-4-propylcyclohexyl)-1-propyloxy]benzoic acid 4-hexylphenyl ester;
4-[3-(trans-4-propylcyclohexyl)-1-propyloxy]benzoic acid 4-heptylphenyl ester;
4-[3-(trans-4-propylcyclohexyl)-1-propyloxy]benzoic acid 4-octylphenyl ester;
4-[3-(trans-4-pentylcyclohexyl)-1-propyloxy]benzoic acid 4-methylphenyl ester;
4-[3-(trans-4-pentylcyclohexyl)-propyloxy]benzoic acid 4-ethylphenyl ester;
4-[3-(trans-4-pentylcyclohexyl)-1-propyloxy]benzoic acid 4-propylphenyl ester;
4-[3-(trans-4-pentylcyclohexyl)-1-propyloxy]benzoic acid 4-butylphenyl ester;
4-[3-(trans-4-pentylcyclohexyl)-1-propyloxy]benzoic acid 4-pentylphenyl ester:
4-[3-(trans-4-pentylcyclohexyl)-1-propyloxy]benzoic acid 4-hexylphenyl ester;
4-[3-(trans-4-pentylcyclohexyl)-1-propyloxy]benzoic acid 4-heptylphenyl ester;
4-[3-(trans-4-pentylcyclohexyl)-1-propyloxy]benzoic acid 4-octylphenyl ester;
4-[3-(trans-4-heptylcyclohexyl)-1-propyloxy]benzoic acid 4-methylphenyl ester;
4-[3-(trans-4-heptylcyclohexyl)-1-propyloxy]benzoic acid 4-ethylphenyl ester;
4-[3-(trans-4-heptylcyclohexyl)-1-propyloxy]benzoic acid 4-propylphenyl ester;
4-[3-(trans-4-heptylcyclohexyl)-1-propyloxy]benzoic acid 4-butylphenyl ester;
4-[3-(trans-4-heptylcyclohexyl)-1-propyloxy]benzoic acid 4-pentylphenyl ester;
4-[3-(trans-4-heptylcyclohexyl)-1-propyloxy]benzoic acid 4-hexylphenyl ester;
4-[3-(trans-4-heptylcyclohexyl)-1-propyloxy]benzoic acid 4-heptylphenyl ester;
4-[3-(trans-4-heptylcyclohexyl)-1-propyloxy]benzoic acid 4-octylphenyl ester;
4-[3-(trans-4-pentylcyclohexyl)-1-propyloxy]benzoic acid 4-methyl 2-fluorophenyl ester;

4-[3-(trans-4-pentylcyclohexyl)-1-propyloxy]benzoic acid 4-ethyl-2-fluorophenyl ester;
4-[3-(trans-4-pentylcyclohexyl)-1-propyloxy]benzoic acid 4-propyl-2-fluorophenyl ester;
4-[3-(trans-4-pentylcyclohexyl)-1-propyloxy]benzoic acid 4-butyl-2-fluorophenyl ester;
4-[3-(trans-4-pentylcyclohexyl)-1-propyloxy]benzoic acid 4-pentyl-2-fluorophenyl ester;
4-[3-(trans-4-pentylcyclohexyl)-1-propyloxy]benzoic acid 4-hexyl-2-fluorophenyl ester;
4-[3-(trans-4-pentylcyclohexyl)-1-propyloxy]benzoic acid 4-heptyl-2-fluorophenyl ester;
4-[3-(trans-4-pentylcyclohexyl)-propyloxy]benzoic acid 4-octyl-2-fluorophenyl ester;
4-[3-(trans-4-pentylcyclohexyl)-1-propyloxy]benzoic acid 4-nonyl-2-fluorophenyl ester;
4-[3-(trans-4-pentylcyclohexyl)-1-propyloxy]benzoic acid 4-decyl-2-fluorophenyl ester;
4-[3-(trans-4-pentylcyclohexyl)-1-propyloxy]benzoic acid 4-methyl-3-fluorophenyl ester;
4-[3-(trans-4-pentylcyclohexyl)-1-propyloxy]benzoic acid 4-ethyl-3-fluorophenyl ester;
4-[3-(trans-4-pentylcyclohexyl)-1-propyloxy]benzoic acid 4-propyl-3-fluorophenyl ester;
4-[3-(trans-4-pentylcyclohexyl)-1-propyloxy]benzoic acid 4-butyl-3-fluorophenyl ester;
4-[3-(trans-4-pentylcyclohexyl)-1-propyloxy]benzoic acid 4-pentyl-3-fluorophenyl ester;
4-[3-(trans-4-pentylcyclohexyl)-1-propyloxy]benzoic acid 4-hexyl-3-fluorophenyl ester;
4-[3-(trans-4-pentylcyclohexyl)-1-propyloxy]benzoic acid 4-heptyl-3-fluorophenyl ester;
4-[3-(trans-4-pentylcyclohexyl)-1-propyloxy]benzoic acid 4-octyl-3-fluorophenyl ester;
4-[3-(trans-4-pentylcyclohexyl)-1-propyloxy]benzoic acid 4-nonyl-3-fluorophenyl ester;
4-[3-(trans-4-pentylcyclohexyl)-1-propyloxy]benzoic acid 4-decyl-3-fluorophenyl ester;
4-[3-(trans-4-pentylcyclohexyl)-1-propyloxy]benzoic acid trans-4-methylcyclohexyl ester;
4-[3-(trans-4-pentylcyclohexyl)-1-propyloxy]benzoic acid trans-4-ethylcyclohexyl ester;
4-[3-(trans-4-pentylcyclohexyl)-1-propyloxy]benzoic acid trans-4-propylcyclohexyl ester;
4-[3-(trans-4-pentylcyclohexyl)-1-propyloxy]benzoic acid trans-4-butylcyclohexyl ester;
4-[3-(trans-4-pentylcyclohexyl)-1-propyloxy]benzoic acid trans-4-pentylcyclohexyl ester, m.p. (C-S$_A$) 64° C., transition S$_A$-N 108° C., cl.p. (N-I) 132° C.;
4-[3-(trans-4-pentylcyclohexyl)-propyloxy]benzoic acid trans-4-hexylcyclohexyl ester;
4-[3-(trans-4-pentylcyclohexyl)-1-propyloxy]benzoic acid trans-4-heptylcyclohexyl ester;
4-[3-(trans-4-pentylcyclohexyl)-1-propyloxy]benzoic acid trans-4-octylcyclohexyl ester;
4-[3-(trans-4-propylcyclohexyl)-1-propyloxy]benzoic acid methyl ester;
4-[3-(trans-4-propylcyclohexyl)-1-propyloxy]benzoic acid ethyl ester;
4-[3-(trans-4-propylcyclohexyl)-1-propyloxy]benzoic acid propyl ester;
4-[3-(trans-4-propylcyclohexyl)-1-propyloxy]benzoic acid butyl ester;
4-[3-(trans-4-propylcyclohexyl)-1-propyloxy]benzoic acid pentyl ester;
4-[3-(trans-4-propylcyclohexyl)-1-propyloxy]benzoic acid hexyl ester;
4-[3-(trans-4-propylcyclohexyl)-1-propyloxy]benzoic acid heptyl ester;
4-[3-(trans-4-propylcyclohexyl)-1-propyloxy]benzoic acid octyl ester;
4-[3-(trans-4-pentylcyclohexyl)-1-propyloxy]benzoic acid methyl ester, m.p. (C-N) 57° C., cl.p. (N-I) 62° C.;
4-[3-(trans-4-pentylcyclohexyl)-1-propyloxy]benzoic acid ethyl ester;
4-[3-(trans-4-pentylcyclohexyl)-1-propyloxy]benzoic acid propyl ester;
4-[3-(trans-4-pentylcyclohexyl)-1-propyloxy]benzoic acid butyl ester;
4-[3-(trans-4-pentylcyclohexyl)-1-propyloxy]benzoic acid pentyl ester;
4-[3-(trans-4-pentylcyclohexyl)-1-propyloxy]benzoic acid hexyl ester;
4-[3-(trans-4-pentylcyclohexyl)-1-propyloxy]benzoic acid heptyl ester;
4-[3-(trans-4-pentylcyclohexyl)-1-propyloxy]benzoic acid octyl ester;
4-[3-(trans-4-heptylcyclohexyl)-1-propyloxy]benzoic acid methyl ester;
4-[3-(trans-4-heptylcyclohexyl)-1-propyloxy]benzoic acid ethyl ester;
4-[3-(trans-4-heptylcyclohexyl)-propyloxy]benzoic acid propyl ester;
4-[3-(trans-4-heptylcyclohexyl)-1-propyloxy]benzoic acid butyl ester;
4-[3-(trans-4-heptylcyclohexyl)-1-propyloxy]benzoic acid pentyl ester;
4-[3-(trans-4-heptylcyclohexyl)-1-propyloxy]benzoic acid hexyl ester;
4-[3-(trans-4-heptylcyclohexyl)-1-propyloxy]benzoic acid heptyl ester;
4-[3-(trans-4-methylcyclohexyl)-1-propyloxy]benzoic acid [(S)-1-methylheptyl] ester;
4-[3-(trans-4-ethylcyclohexyl)-1-propyloxy]benzoic acid [(S)-1-methylheptyl] ester;
4-[3-(trans-4-propylcyclohexyl)-1-propyloxy]benzoic acid [(S)-1-methylheptyl] ester;
4-[3-(trans-4-butylcyclohexyl)-1-propyloxy]benzoic acid [(S)-1-methylheptyl] ester;
4-[3-(trans-4-pentylcyclohexyl)-1-propyloxy]benzoic acid [(S)-1-methylheptyl] ester;
4-[3-(trans-4-hexylcyclohexyl)-1-propyloxy]benzoic acid [(S)-1-methylheptyl] ester;
4-[3-(trans-4-heptylcyclohexyl)-1-propyloxy]benzoic acid [(S)-1-methylheptyl] ester;
4-[3-(trans-4-octylcyclohexyl)-1-propyloxy]benzoic acid [(S)-1-methylheptyl] ester;
4-[3-(trans 4-nonylcyclohexyl)-1-propyloxy]benzoic acid [(S)-1-methylheptyl] ester;
4-[3-(trans-4-decylcyclohexyl)-1-propyloxy]benzoic acid [(S)-1-methylheptyl] ester.

EXAMPLE 5

A mixture of 0.3 g of trans-4-pentylcyclohexanol, 0.5 g of 3-(trans-4-pentylcyclohexyl; 1-propyl bromide, 1.0 g of potassium carbonate and 50 ml of absolute cyclohexanone is heated under reflux for 7 days. Subsequently, the batch is worked-up and purified in an analogous manner to Example 1. This gives 0.5 g of trans-4-pentylcyclohexyl 3-(trans-4-pentylcyclohexyl)-1-propyl ether; m.p. (C-S$_B$) 36° C., cl.p. (S$_B$-I) 42° C.

The following compounds can be prepared in an analogous manner:

trans-4-propylcyclohexyl 3-(trans-4-methylcyclohexyl)-1-propyl ether;
trans-4-propylcyclohexyl 3-(trans-4-ethylcyclohexyl)-1-propyl ether;
trans-4-propylcyclohexyl 3-(trans-4-propylcyclohexyl)-1-propyl ether;
trans-4-propylcyclohexyl 3-(trans-4-butylcyclohexyl)-1-propyl ether;
trans-4-propylcyclohexyl 3 (trans-4-pentylcyclohexyl)-1-propyl ether;
trans-4-propylcyclohexyl 3-(trans-4-hexylcyclohexyl)-1-propyl ether;
trans-4-propylcyclohexyl 3-(trans-4-heptylcyclohexyl)-1-propyl ether;
trans-4-pentylcyclohexyl 3-(trans-4-methylcyclohexyl)-1-propyl ether;
trans-4-pentylcyclohexyl 3-(trans-4-ethylcyclohexyl)-1-propyl ether;
trans-4-pentylcyclohexyl 3-(trans-4-propylcyclohexyl)-1-propyl ether;
trans-4-pentylcyclohexyl 3-(trans-4-butylcyclohexyl)-1-propyl ether;
trans-4-pentylcyclohexyl 3-(trans-4-hexylcyclohexyl)-1-propyl ether;
trans-4-pentylcyclohexyl 3-(trans-4-heptylcyclohexyl)-1-propyl ether;
trans-4-heptylcyclohexyl 3-(trans-4-methylcyclohexyl)-1-propyl ether;
trans-4-heptylcyclohexyl 3-(trans-4-ethylcyclohexyl)-1-propyl ether;
trans-4-heptylcyclohexyl 3-(trans-4-propylcyclohexyl)-1-propyl ether;
trans-4-heptylcyclohexyl 3-(trans-4-butylcyclohexyl)-1-propyl ether;
trans-4-heptylcyclohexyl 3-(trans-4-pentylcyclohexyl)-1-propyl ether;
trans-4-heptylcyclohexyl 3-(trans-4-hexylcyclohexyl)-1-propyl ether;
trans-4-heptylcyclohexyl 3-(trans-4-heptylcyclohexyl)-1-propyl ether;
trans-4-cyanocyclohexyl 3-(trans-4-methylcyclohexyl)-1-propyl ether;
trans-4-cyanocyclohexyl 3-(trans-4-ethylcyclohexyl)-1-propyl ether;
trans-4-cyanocyclohexyl 3-(trans-4-propylcyclohexyl)-1-propyl ether;
trans-4-cyanocyclohexyl 3-(trans-4-butylcyclohexyl)-1-propyl ether;
trans-4-cyanocyclohexyl 3-(trans-4-pentylcyclohexyl)-1-propyl ether;
trans-4-cyanocyclohexyl 3-(trans-4-hexylcyclohexyl)-1-propyl ether;
trans-4-cyanocyclohexyl 3-(trans-4-heptylcyclohexyl)-1-propyl ether;
trans-4-cyanocyclohexyl 3-(trans-4-octylcyclohexyl)-1-propyl ether;
trans-4-cyanocyclohexyl 3-(trans-4-nonylcyclohexyl)-1-propyl ether;
trans-4-cyanocyclohexyl 3-(trans-4-decylcyclohexyl)-1-propyl ether;
trans-4-(trans-4-propylcyclohexyl)cyclohexyl 3-(trans-4-propylcyclohexyl)-1-propyl ether;
trans-4-(trans-4-pentylcyclohexyl)cyclohexyl 3-(trans-4-propylcyclohexyl)-1-propyl ether;
trans-4-(trans-4-heptylcyclohexyl)cyclohexyl 3-(trans-4-propylcyclohexyl)-1-propyl ether;
trans-4-(trans-4-propylcyclohexyl)cyclohexyl 3-(trans-4-pentylcyclohexyl)-1-propyl ether;
trans-4-(trans-4-pentylcyclohexyl)cyclohexyl 3-(trans-4-pentylcyclohexyl)-1-propyl ether;
trans-4-(trans-4-heptylcyclohexyl)cyclohexyl 3-(trans-4-pentylcyclohexyl)-1-propyl ether;
trans-4-(trans-4-propylcyclohexyl)cyclohexyl 3-(trans-4-heptylcyclohexyl)-1-propyl ether;
trans-4-(trans-4-pentylcyclohexyl)cyclohexyl 3-(trans-4-heptylcyclohexyl)-1-propyl ether;
trans-4-(trans-4-heptylcyclohexyl)cyclohexyl 3-(trans-4-heptylcyclohexyl)-1-propyl ether;
3-(trans-4-methylcyclohexyl)-1-propyl trans-4-(4-cyanophenyl)cyclohexyl ether;
3-(trans-4-ethylcyclohexyl)-1-propyl trans-4-(4-cyanophenyl)cyclohexyl ether;
3-(trans-4-propylcyclohexyl)-1-propyl trans-4-(4-cyanophenyl)cyclohexyl ether;
3-(trans-4-butylcyclohexyl)-1-propyl trans-4-(4-cyanophenyl)cyclohexyl ether;
3-(trans-4-pentylcyclohexyl)-1-propyl trans-4-(4-cyanophenyl)cyclohexyl ether;
3-(trans-4-hexylcyclohexyl)-1-propyl trans-4-(4-cyanophenyl)cyclohexyl ether;
3-(trans-4-heptylcyclohexyl)-1-propyl trans-4-(4-cyanophenyl)cyclohexyl ether;
3-(trans-4-octylcyclohexyl)-1-propyl trans-4-(4-cyanophenyl)cyclohexyl ether;
3-(trans-4-nonylcyclohexyl)-1-propyl trans-4-(4-cyanophenyl)cyclohexyl ether;
3-(trans-4-decylcyclohexyl)-1-propyl trans-4-(4-cyanophenyl)cyclohexyl ether;
3-(trans-4-methylcyclohexyl)-1-propyl trans-4-(4-propylphenyl)cyclohexyl ether;
3-(trans-4-ethylcyclohexyl).1-propyl trans-4-(4-propylphenyl)cyclohexyl ether;
3-(trans-4-propylcyclohexyl) 1-propyl trans-4-(4-propylphenyl)cyclohexyl ether;
3-(trans-4-butylcyclohexyl)-1-propyl trans-4-(4-propylphenyl)cyclohexyl ether;
3-(trans-4-pentylcyclohexyl)-1-propyl trans-4-(4-propylphenyl)cyclohexyl ether;
3-(trans-4-hexylcyclohexyl)-1-propyl trans-4-(4-propylphenyl)cyclohexyl ether;
3-(trans-4-heptylcyclohexyl)-1-propyl trans-4-(4-propylphenyl)cyclohexyl ether;
3-(trans-4-octylcyclohexyl)-1-propyl trans-4-(4-propylphenyl)cyclohexyl ether;
3-(trans-4-nonylcyclohexyl)-1-propyl trans-4-(4-propylphenyl)cyclohexyl ether;
3-(trans-4-decylcyclohexyl)-1-propyl trans-4-(4-propylphenyl)cyclohexyl ether;
3-(trans-4-methylcyclohexyl)-1-propyl trans-4-(4-pentylphenyl)cyclohexyl ether;
3-(trans-4-ethylcyclohexyl)-1-propyl trans-4-(4-pentylphenyl)cyclohexyl ether;
3-(trans-4-propylcyclohexyl)-1-propyl trans-4-(4-pentylphenyl)cyclohexyl ether;
3-(trans-4-butylcyclohexyl)-1-propyl trans-4-(4-pentylphenyl)cyclohexyl ether;
3-(trans 4-pentylcyclohexyl)-1-propyl trans-4-(4-pentylphenyl)cyclohexyl ether;
3-(trans-4-hexylcyclohexyl)-1-propyl trans-4-(4-pentylphenyl)cyclohexyl ether;
3-(trans-4-heptylcyclohexyl)-1-propyl trans-4-(4-pentylphenyl)cyclohexyl ether;
3-(trans-4-octylcyclohexyl)-1-propyl trans-4-(4-pentylphenyl)cyclohexyl ether;
3-(trans-4-nonylcyclohexyl)-1-propyl trans-4-(4-pentylphenyl)cyclohexyl ether;

3-(trans-4-decylcyclohexyl)-1-propyl trans-4-(4-pentyl-phenyl)cyclohexyl ether;

3-(trans-4-methylcyclohexyl)-1-propyl trans-4-4-heptyl-phenyl)cyclohexyl ether;

3-(trans-4-ethylcyclohexyl)-1-propyl trans-4-(4 -heptyl-phenyl)cyclohexyl ether;

3-(trans-4-propylcyclohexyl)-1-propyl trans-4-(4-heptylphenyl)cyclohexyl ether;

3-(trans-4-butylcyclohexyl)-1-propyl trans-4-(4-heptyl-phenyl)cyclohexyl ether;

3-(trans-4-pentylcyclohexyl)-1-propyl trans-4-(4-heptylphenyl)cyclohexyl ether;

3-(trans-4-hexylcyclohexyl)-1-propyl trans 4-(4-heptyl-phenyl)cyclohexyl ether;

3-(trans-4-heptylcyclohexyl)-1-propyl trans-4-(4-heptylphenyl)cyclohexyl ether;

3-(trans-4-octylcyclohexyl)-1-propyl trans-4-(4-heptyl-phenyl)cyclohexyl ether;

3-(trans-4-nonylcyclohexyl)-1-propyl trans-4-(4-heptyl-phenyl)cyclohexyl ether;

3-(trans-4-decylcyclohexyl)-1-propyl trans-4-(4-heptyl-phenyl)cyclohexyl ether.

EXAMPLE 6

A mixture of 0.1 g of sodium hydride and 25 ml of tetrahydrofuran was treated with 0.5 g of trans-4-pentylcyclohexanol while gassing with nitrogen, the mixture was stirred for 2 hours, then treated with 1.0 g of 3-(trans-4-pentylcyclohexyl)-1-propyl bromide and subsequently heated at 70° C. overnight. Subsequently, the mixture was worked-up and purified in an analogous manner to Example 1. This gave 0.7 g of trans-4-pentylcyclohexyl 3-(trans-4-pentylcyclohexyl)-1-propyl ether; m.p. (C-S$_B$) 36° C., cl.p. (S$_B$-I) 42° C.

The following compound was prepared in an analogous manner:

trans-4-[2-(trans-4-propylcyclohexyl)ethyl]cyclohexyl 3-(trans-4-pentylcyclohexyl)-1-propyl ether, m.p. (C-S$_B$) 58° C., cl.p. (S$_B$-I) 129° C.

The compounds referred to in Example 5 can also be prepared in an analogous manner.

I claim:

1. A compound of the formula:

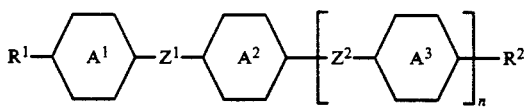

wherein $Z^1$ is a group —CH$_2$—CH$_2$—CH$_2$O—; M stands for the number 0 or 1; $R^1$ is a group $R^3$ or $R^3$—A$^4$—$Z^3$—; $R^2$ is a group $R^4$; $Z^2$ and $Z^3$ each independently is a single covalent bond, —CH$_2$—CH$_2$—, —COO—, or —OOC; $A^1$ and $A^4$ each are trans-1,4-cyclohexylene; $A^2$ and $A^3$ are 1,4-phenylene unsubstituted or substituted with halogen, in which optionally 1 to 2 CH groups are replaced by nitrogen, or trans-1,4-cyclohexylene in which optionally 2 CH$_2$ groups are replaced by oxygen; $R^3$ and $R^4$ each independently is an C$_2$-C$_{18}$ alkyl or an C$_2$-C$_{18}$ alkenyl group, the alkyl and the alkenyl group being unsubstituted or substituted with halogen in which optionally either 1 CH$_2$ group or 2 non-adjacent CH$_2$ groups are replaced by at least one of —O—, —COO—, or —OOC—, or one of the groups of $R^3$ and $R^4$ is halogen or cyano.

2. A compound according to claim 1, wherein $A^3$ is 1,4-phenylene or trans-1,4-cyclohexylene.

3. A compound according to claim 1, wherein the group $A^3$ is 1,4-phenylene substituted with halogen or trans-1,4-cyclohexylene.

4. A compound according to claim 1, wherein the group $A^3$ is 1,4-phenylene in which 1 to 2 groups are replaced by nitrogen, or trans-1,4-cyclohexylene having 2 CH$_2$ groups replaced by oxygen.

5. A compound according to claim 1, wherein at least one of the groups $A^1$, $A^2$, $A^3$ or $A^4$ is 1,4-phenylene substituted with halogen, or trans-1,4-cyclohexylene; at least one of the groups $A^1$, $A^2$, $A^3$ or $A^4$ is 1,4-phenylene in which 1 or 2 CH groups are replaced by nitrogen or, trans 1,4-cyclohexylene having 2 CH$_2$ groups replaced by oxygen and the other of the groups $A^1$, $A^2$, $A^3$ and $A^4$ each independently is 1,4-phenylene or trans-1,4-cyclohexylene.

6. A compound according to claim 1, wherein one of the groups $Z^2$, $Z^3$ and $Z^4$ is a single covalent bond, —CH$_2$CH$_2$—, —COO—, or —OOC—; while the other group is at least one of a single covalent bond, —COO— or —OOC—.

7. A compound according to claim 1, wherein $Z^1$ is the group —CH$_2$CH$_2$CH$_2$O— and $A^1$ is a saturated ring.

8. A compound according to claim 1, of the formula

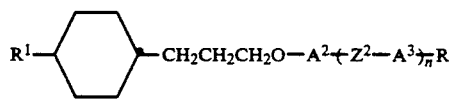

IA wherein $A^2$, $A^3$, $R^1$, $R^2$, $Z^2$ and n are as described in claim 7.

9. A compound according to claim 1, of the formulas

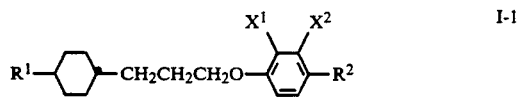

I-1

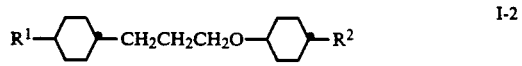

I-2

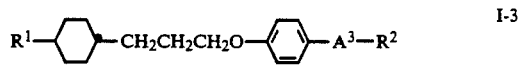

I-3

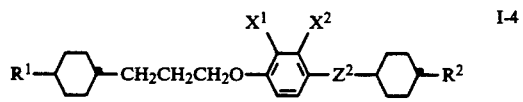

I-4

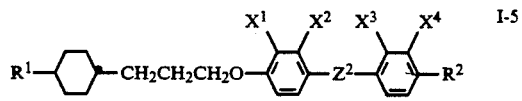

I-5

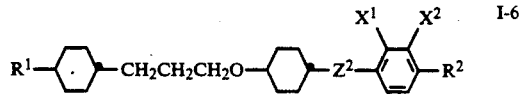

I-6

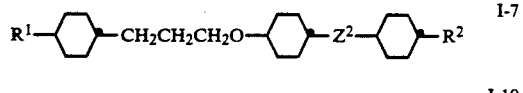

I-7

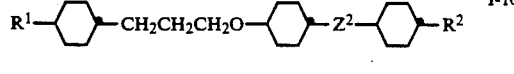

I-10

-continued and $$R^1-\underset{\underset{X^1}{\big|}}{\overset{\overset{X^2}{\big|}}{\text{Ar}}}-OCH_2CH_2CH_2-\text{Cy}-Z^2-\text{Cy}-R^2 \quad \text{I-11}$$

wherein $A^3$, $R^1$, $R^2$, $R^4$ and $Z^2$ are as described in claim 11 and $X^1$, $X^2$, $X^3$ and $X^4$ each independently are hydrogen or halogen.

10. A compound according to claim 9, wherein $X^1$, $X^2$, $X^3$ and $X^4$ each independently are at least one of hydrogen or fluorine.

11. A compound according to claim 9, wherein $R^1$ is a group $R^3$, and $R^2$ is a group $R^4$.

12. A compound according to claim 11, wherein $R^3$ and $R^4$ each have a maximum of 10 carbon atoms.

13. A compound according to claim 11, wherein $R^3$ and $R^4$ each independently are an alkyl or an alkenyl group, said alkyl and alkenyl groups being unsubstituted or substituted with halogen in which optionally either 1 $CH_2$ group or 2 non-adjacent $CH_2$ groups is replaced by at least one of —O—, —COO— or —OOC—, and in each case $R^3$ and $R^4$ have a maximum of 12 carbon atoms, or one of $R^3$ and $R^4$ is halogen or cyano.

14. A compound according to claim 13, wherein $R^3$ and $R^4$ have in each case a maximum of 7 carbon atoms.

15. A compound according to claim 13, wherein $R^3$ is alkyl, alkenyl, alkoxy, alkenyloxy, alkoxycarbonyl, alkenyloxycarbonyl, alkanoyloxy or alkenoyloxy, and $R^4$ is alkyl, alkenyl, alkoxy, alkenyloxy, alkoxycarbonyl, alkenyloxycarbonyl, alkanoyloxy, alkenoyloxy, halogen or cyano.

16. A compound according to claim 13, wherein $R^3$ and $R^4$ each independently are an $C_1$-$C_{18}$-alkyl or an $C_2$-$C_{18}$-alkenyl group, said groups being unsubstituted or substituted with halogen in which optionally either 1 $CH_2$ group or 2 non-adjacent $CH_2$ groups are replaced by at least one of —O—, —COO— or —OOC—, and the sum of the carbon atoms in $R^3$ and $R^4$ together is at least 10.

17. A compound according to claim 16, wherein the sum of the carbon atoms in $R^3$ and $R^4$ together is at least 12.

18. A compound according to claim 17, wherein $R^3$ and $R^4$ each independently are alkyl, alkenyl, alkoxy, alkenyloxy, alkoxycarbonyl, alkenyloxycarbonyl, alkanoyloxy, or alkenoyloxy.

19. A compound according to claim 1, of the formula $$R^1-\text{A}^1-Z^1-\text{A}^2-R^2$$

wherein
$R^1$ is $R^3$—$A^4$—$Z^3$—;
$R^3$ is alkyl;
$A^4$ is trans-1,4-cyclohexylene;
$Z^3$ is a single covalent bond;
$A^1$ is trans-1,4-cyclohexylene;
$Z^1$ is —$CH_2$—$CH_2$—$CH_2O$—;
$A^2$ is 1,4-phenylene substituted with halogen;
$R^2$ is $R^4$; and $R^4$ is alkyl in which one $CH_2$ group is replaced by —O—

20. A compound according to claim 19 of the formula:

$$C_3H_7-\text{Cy}-\text{Cy}-CH_2CH_2-O-\underset{\underset{F}{\big|}}{\overset{\overset{F}{\big|}}{\text{Ar}}}-OC_2H_5$$

21. A liquid crystalline mixture having at least 2 components, wherein at least one component is a compound of formula $$R^1-\text{A}^1-Z^1-\text{A}^2-[Z^2-\text{A}^3]_n-R^2 \quad \text{I}$$

wherein $Z^1$ is a group —$CH_2$—$CH_2$—$CH_2O$—; n stands for the number 0 or 1; $R^1$ is a group $R^3$ or $R^3$—$A^4$—$Z^3$—; $R^2$ is a group $R^4$; $Z^2$ and $Z^3$ each independently is a single covalent bond, —$CH_2$—$CH_2$—, —COO—, or —OOC; $A^1$ and $A^4$ each are trans-1,4-cyclohexylene; $A^2$ and $A^3$ are 1,4-phenylene unsubstituted or substituted with halogen, in which optionally 1 to 2 CH groups are replaced by nitrogen, or trans-1,4-cyclohexylene in which optionally 2 $CH_2$ groups are replaced by oxygen; $R^3$ and $R^4$ each independently is an $C_1$-$C_{18}$ alkyl or an $C_2$-$C_{18}$ alkenyl group, the alkyl and the alkenyl group being unsubstituted or substituted with halogen in which optionally either 1 $CH_2$ group or 2 non-adjacent $CH_2$ groups are replaced by at least one of —O—, —COO—, or —OOC—, or one of the groups of $R^3$ and $R^4$ is halogen or cyano.

22. The liquid crystalline mixture according to claim 21, wherein an amount of the compound of formula I is 1–60 wt. % of the total amount of the mixture.

23. An electro-optical cell comprising:
a) two plate means;
b) a liquid crystal means disposed between the two plate means and including a compound of formula $$R^1-\text{A}^1-Z^1-\text{A}^2-[Z^2-\text{A}^3]_n-R^2 \quad \text{I}$$

wherein $Z^1$ is a group —$CH_2$—$CH_2$—$CH_2O$—; n stands for the number 0 or 1; $R^1$ is a group $R^3$ or $R^3$—$A^4$—$Z^3$—; $R^2$ is a group $R^4$; $Z^2$ and $Z^3$ each independently is a single covalent bond, —$CH_2$—$CH_2$—, —COO—, or —OOC; $A^1$ and $A^4$ each are trans-1,4-cyclohexylene; $A^2$ and $A^3$ are 1,4-phenylene unsubstituted or substituted with halogen, in which optionally 1 to 2 CH groups are replaced by nitrogen, or trans-1,4-cyclohexylene in which optionally 2 $CH_2$ groups are replaced by oxygen; $R^3$ and $R^4$ each independently is an alkyl $C_1$-$C_{18}$ or an $C_2$-$C_{18}$ alkenyl group, the alkyl and the alkenyl group being unsubstituted or substituted with halogen in which optionally either 1 $CH_2$ group or 2 non-adjacent $CH_2$ groups are replaced by at least one of —O—, —COO—, or —OOC—, or one of the groups of $R^3$ and $R^4$ is halogen or cyano; and
c) means for applying an electrical potential to said plate means.

* * * * *

UNITED STATES PATENT AND TRADEMARK OFFICE
CERTIFICATE OF CORRECTION

PATENT NO. : 5,238,600
DATED : August 24, 1993
INVENTOR(S) : Stephen Kelly

It is certified that error appears in the above-indentified patent and that said Letters Patent is hereby corrected as shown below:

On the title page: Item [54] and Column 1, line 1,

Delete "IBIMETHYLENOXY" and insert -- TRIMETHYLENOXY --

In the claims:

Claim 1, col. 45, line 51, delete "M" and insert -- n --.

Claim 4, col. 46, line 5, after "2" insert -- CH --.

Claim 6, col. 46, line 18, after "$z^2$" delete "," and insert -- and --;

Claim 6, col. 46, line 18, after "$z^3$" delete "and $z^4$".

Claim 23, col. 48, line 59, delete "alkyl $C_1$-$C_{18}$" and insert

-- $C_1$-$C_{18}$ alkyl --.

Signed and Sealed this

Twenty-fourth Day of October, 1995

Attest:

BRUCE LEHMAN

Attesting Officer

Commissioner of Patents and Trademarks